(12) United States Patent
Shelton, IV et al.

(10) Patent No.: US 10,610,226 B2
(45) Date of Patent: Apr. 7, 2020

(54) METHODS AND DEVICES FOR SEALING STAPLED TISSUE

(71) Applicant: Ethicon Endo-Surgery, Inc., Cincinnati, OH (US)

(72) Inventors: Frederick E. Shelton, IV, Hillsboro, OH (US); Jason L. Harris, Lebanon, OH (US); Jeffrey S. Swayze, Hamilton, OH (US); Mark S. Zeiner, Mason, OH (US); Thomas Lee Craven, Bridgewater, NJ (US); Anne J. Gorman, Highstown, NJ (US); Bret W. Smith, Kings Mills, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 95 days.

(21) Appl. No.: 14/300,799

(22) Filed: Jun. 10, 2014

(65) Prior Publication Data

US 2015/0351761 A1    Dec. 10, 2015

(51) Int. Cl.
*A61B 17/10* (2006.01)
*A61B 17/068* (2006.01)
(Continued)

(52) U.S. Cl.
CPC ...... *A61B 17/105* (2013.01); *A61B 17/00491* (2013.01); *A61B 17/064* (2013.01);
(Continued)

(58) Field of Classification Search
CPC ...... A61B 17/068–17/07292; A61B 17/00491; A61B 2017/1157
See application file for complete search history.

(56) References Cited

U.S. PATENT DOCUMENTS 5,290,552 A * 3/1994 Sierra ............... A61L 24/0005
424/423
5,503,638 A    4/1996 Cooper et al.
(Continued)

FOREIGN PATENT DOCUMENTS

CN    1386477 A    12/2002
CN    101019775 A    8/2007
(Continued)

OTHER PUBLICATIONS

Chen et al. "Elastomeric Biomaterials for Tissue Engineering." Prog. Polymer. Sci. 38(2013):584-671.
(Continued)

*Primary Examiner* — Shaun L David
(74) *Attorney, Agent, or Firm* — Mintz Levin Cohn Ferris Glovsky and Popeo, P.C.

(57) ABSTRACT

Adjunct material and methods of using adjunct material to reinforce a staple line are provided herein. In general, adjunct material can be used to maintain a seal in tissue and prevent stapled tissue from tearing. This adjunct material can be coupled to a jaw of a surgical stapler, and can be deployed into tissue along with the staples. In some embodiments, the adjunct material can be sized and shaped so that a portion of the material extends laterally outside of the staple line and distributes strain to tissue outside of the staple line. In certain aspects, sealant can be applied to the staple line and to the adjunct material in various ways to further seal the tissue and/or prevent leaks from forming in the tissue.

20 Claims, 35 Drawing Sheets

(51) Int. Cl.
*A61B 17/064* (2006.01)
*A61B 17/00* (2006.01)
*A61B 17/072* (2006.01)
*A61B 17/115* (2006.01)

(52) U.S. Cl.
CPC ........ *A61B 17/068* (2013.01); *A61B 17/0644* (2013.01); *A61B 17/07207* (2013.01); *A61B 17/07292* (2013.01); *A61B 17/1155* (2013.01); *A61B 2017/00004* (2013.01); *A61B 2017/00884* (2013.01); *A61B 2017/00893* (2013.01); *A61B 2017/00964* (2013.01); *A61B 2017/0641* (2013.01); *A61B 2017/0688* (2013.01); *A61B 2017/07228* (2013.01); *A61B 2017/07235* (2013.01); *A61B 2017/07242* (2013.01); *A61B 2017/07271* (2013.01)

(56) References Cited

U.S. PATENT DOCUMENTS

| | | | |
|---|---|---|---|
| 5,542,594 | A | 8/1996 | McKean et al. |
| 5,690,675 | A * | 11/1997 | Sawyer ............ A61B 17/00491 128/898 |
| 5,698,213 | A | 12/1997 | Jamiolkowski et al. |
| 5,700,583 | A | 12/1997 | Jamiolkowski et al. |
| 5,766,188 | A | 6/1998 | Igaki |
| 5,769,892 | A | 6/1998 | Kingwell |
| 5,810,855 | A | 9/1998 | Rayburn et al. |
| 5,814,057 | A | 9/1998 | Oi et al. |
| 5,843,096 | A | 12/1998 | Igaki et al. |
| 5,887,755 | A | 3/1999 | Hood, III |
| 5,902,312 | A | 5/1999 | Frater et al. |
| 6,273,897 | B1 | 8/2001 | Dalessandro et al. |
| 7,143,924 | B2 | 12/2006 | Scirica et al. |
| 7,143,925 | B2 | 12/2006 | Shelton, IV et al. |
| 7,547,312 | B2 * | 6/2009 | Bauman ............ A61B 17/072 227/175.1 |
| 7,772,352 | B2 | 8/2010 | Bezwada |
| 8,317,070 | B2 | 11/2012 | Hueil et al. |
| 8,393,514 | B2 | 3/2013 | Shelton, IV et al. |
| 8,551,058 | B2 | 10/2013 | Measamer et al. |
| 2002/0165559 | A1 * | 11/2002 | Grant ............ A61B 17/07207 606/139 |
| 2003/0135238 | A1 * | 7/2003 | Milbocker ............ A61L 24/046 606/231 |
| 2003/0181917 | A1 | 9/2003 | Gertner |
| 2005/0245965 | A1 * | 11/2005 | Orban, III ............ A61B 17/068 606/214 |
| 2006/0025816 | A1 | 2/2006 | Shelton |
| 2006/0085031 | A1 * | 4/2006 | Bettuchi .......... A61B 17/00491 606/215 |
| 2006/0085032 | A1 * | 4/2006 | Viola .................... A61B 17/115 606/219 |
| 2006/0085033 | A1 * | 4/2006 | Criscuolo ........ A61B 17/00491 606/219 |
| 2006/0135992 | A1 * | 6/2006 | Bettuchi ............. A61B 17/072 606/219 |
| 2006/0178683 | A1 | 8/2006 | Shimoji et al. |
| 2006/0212050 | A1 * | 9/2006 | D'Agostino ......... A61B 17/072 606/151 |
| 2006/0257458 | A1 | 11/2006 | Gorman et al. |
| 2007/0005007 | A1 | 1/2007 | Hoogenakker et al. |
| 2007/0203510 | A1 * | 8/2007 | Bettuchi .............. A61B 17/115 606/153 |
| 2007/0225645 | A1 | 9/2007 | Tarinelli |
| 2007/0246505 | A1 | 10/2007 | Pace-Floridia et al. |
| 2008/0140115 | A1 * | 6/2008 | Stopek ................. A61B 17/068 606/219 |
| 2008/0308608 | A1 | 12/2008 | Prommersberger |
| 2009/0076510 | A1 | 3/2009 | Bell et al. |
| 2009/0120994 | A1 * | 5/2009 | Murray ............ A61B 17/00491 227/180.1 |
| 2009/0234193 | A1 | 9/2009 | Weisenburgh, II et al. |
| 2009/0270686 | A1 | 10/2009 | Duke et al. |
| 2009/0277947 | A1 | 11/2009 | Viola |
| 2010/0016888 | A1 * | 1/2010 | Calabrese ............ A61B 17/072 606/219 |
| 2010/0087840 | A1 | 4/2010 | Ebersole et al. |
| 2010/0147921 | A1 | 6/2010 | Olson |
| 2011/0192882 | A1 | 8/2011 | Hess et al. |
| 2011/0245866 | A1 | 10/2011 | Cassingham et al. |
| 2012/0024934 | A1 | 2/2012 | Shelton, IV et al. |
| 2012/0080335 | A1 | 4/2012 | Shelton, IV et al. |
| 2012/0083835 | A1 | 4/2012 | Shelton, IV et al. |
| 2012/0145767 | A1 | 6/2012 | Shah et al. |
| 2012/0241491 | A1 | 9/2012 | Aldridge et al. |
| 2012/0241492 | A1 | 9/2012 | Shelton, IV et al. |
| 2012/0241493 | A1 | 9/2012 | Baxter, III et al. |
| 2012/0241498 | A1 | 9/2012 | Gonzalez et al. |
| 2012/0241499 | A1 | 9/2012 | Baxter, III et al. |
| 2012/0241500 | A1 | 9/2012 | Timmer et al. |
| 2012/0241501 | A1 | 9/2012 | Swayze et al. |
| 2012/0241503 | A1 | 9/2012 | Baxter, III et al. |
| 2012/0241505 | A1 | 9/2012 | Alexander, III et al. |
| 2012/0248169 | A1 | 10/2012 | Widenhouse et al. |
| 2012/0318844 | A1 | 12/2012 | Shelton, IV et al. |
| 2013/0068816 | A1 * | 3/2013 | Mandakolathur Vasudevan et al. ................. A61B 17/07292 227/175.1 |
| 2013/0075447 | A1 * | 3/2013 | Weisenburgh, II .......................... A61B 17/00491 227/176.1 |
| 2013/0112733 | A1 | 5/2013 | Aranyi et al. |
| 2013/0146642 | A1 | 6/2013 | Shelton, IV et al. |
| 2013/0153638 | A1 | 6/2013 | Carter et al. |
| 2013/0153641 | A1 | 6/2013 | Shelton, IV et al. |
| 2013/0161374 | A1 | 6/2013 | Swayze et al. |
| 2013/0209659 | A1 | 8/2013 | Racenet et al. |
| 2013/0256365 | A1 | 10/2013 | Shelton, IV et al. |
| 2013/0256372 | A1 | 10/2013 | Baxter, III et al. |
| 2013/0256373 | A1 | 10/2013 | Schmid et al. |
| 2013/0256376 | A1 | 10/2013 | Barton et al. |
| 2013/0256377 | A1 | 10/2013 | Schmid et al. |
| 2013/0256380 | A1 | 10/2013 | Schmid et al. |
| 2014/0021242 | A1 | 1/2014 | Hodgkinson et al. |
| 2014/0155916 | A1 * | 6/2014 | Hodgkinson .......... A61F 2/0063 606/151 |
| 2014/0158741 | A1 | 6/2014 | Woodard, Jr. et al. |
| 2014/0166721 | A1 * | 6/2014 | Stevenson ........ A61B 17/07292 227/176.1 |
| 2014/0252068 | A1 | 9/2014 | Shelton, IV et al. |
| 2015/0173756 | A1 | 6/2015 | Baxter, III et al. |
| 2015/0272575 | A1 | 10/2015 | Leimbach et al. |
| 2015/0351753 | A1 | 12/2015 | Shelton, IV et al. |

FOREIGN PATENT DOCUMENTS

| | | |
|---|---|---|
| CN | 101156798 A | 4/2008 |
| CN | 101164501 A | 4/2008 |
| CN | 101370433 A | 2/2009 |
| CN | 102641145 A | 8/2012 |
| CN | 102933243 A | 2/2013 |
| WO | WO-90074 A2 | 2/2000 |
| WO | 14016819 A1 | 1/2014 |

OTHER PUBLICATIONS

Lim et al. "Fabrication and Evaluation of Poly(epsilon-caprolactone)/Silk Fibroin Blend Nanofibrous Scaffold." Biopolymers. 97(2012):265-275.
U.S. Appl. No. 13/763,192 filed Feb. 8, 2013.
U.S. Appl. No. 14/074,810 filed Nov. 8, 2013.
U.S. Appl. No. 14/074,884 filed Nov. 8, 2013.
U.S. Appl. No. 14/074,902 filed Nov. 8, 2013.
U.S. Appl. No. 14/075,438 filed Nov. 8, 2013.
U.S. Appl. No. 14/075,459 filed Nov. 8, 2013.
U.S. Appl. No. 14/300,793 filed Jun. 10, 2014.
U.S. Appl. No. 14/300,801 filed Jun. 10, 2014.
U.S. Appl. No. 14/300,804 filed Jun. 10, 2014.

(56) References Cited

OTHER PUBLICATIONS

U.S. Appl. No. 14/300,807 filed Jun. 10, 2014.
U.S. Appl. No. 14/300,811 filed Jun. 10, 2014.
U.S. Appl. No. 14/300,815 filed Jun. 10, 2014.
U.S. Appl. No. 14/300,817 filed Jun. 10, 2014.
U.S. Appl. No. 14/300,819 filed Jun. 10, 2014.
U.S. Appl. No. 14/300,820 filed Jun. 10, 2014.
U.S. Appl. No. 14/300,954 filed Jun. 10, 2014.
Zhao et al. "Biodegradable Fibrous Scaffolds Composed of Gelatin Coated Poly(?-caprolactone) Prepared by Coaxial Elecrospinning." J. Biomed. Mater. Res. 83A(2007):372-382.
European Search Report for EP15171473.0 dated Aug. 24, 2015.
International Search Report for PCT/US2015/030683 dated Oct. 19, 2015.
International Search Report for PCT/US2015/032513 dated Aug. 14, 2015.
Chinese Search Report for CN PCT Application No. 2015800429310 (11 pages).

* cited by examiner

METHODS AND DEVICES FOR SEALING STAPLED TISSUE

FIELD

The subject matter disclosed herein relates to methods and devices for reinforcing a staple line.

BACKGROUND

Surgical staplers are used in surgical procedures to seal, divide, and/or transect tissues in the body by closing openings in tissue, blood vessels, ducts, shunts, or other objects or body parts involved in the particular procedure. The openings can be naturally occurring, such as passageways in blood vessels, airways or an internal lumen or organ like the stomach, or they can be formed by the surgeon during a surgical procedure, such as by puncturing tissue or blood vessels to form a bypass or an anastomosis, or by cutting tissue during a stapling procedure.

Most staplers have a handle with an elongate flexible or rigid shaft having a pair of opposed jaws formed on an end thereof for holding and forming staples therebetween. At least one of the opposed jaws is movable relative to the other jaw. In the case of laparoscopic surgery, often one jaw is fixed and the other is movable. In some devices (for example an open linear stapler), the opposed jaws can be separated by the operator and reassembled providing the relative motion needed for tissue placement. The staples are typically contained in a staple cartridge, which can house multiple rows of staples and is often disposed in one of the two jaws for ejection of the staples to the surgical site. In use, the jaws are positioned so that the object to be stapled is disposed between the jaws, and staples are ejected and formed when the jaws are closed and the device is actuated. Some staplers include a knife configured to travel between rows of staples in the staple cartridge to longitudinally cut the stapled tissue between the stapled rows. Placement of the device, manipulation of components or systems of the device, and other actuations of the device such as articulation, firing, etc. can be accomplished in a variety of ways, such as electromechanically, mechanically, or hydraulically.

While surgical staplers have improved over the years, a number of problems can potentially arise. Although rare, as illustrated in FIG. 1, one problem is that leaks can occur due to staples S forming tears H when penetrating a tissue T or other object in which the staples S are disposed. Blood, air, gastrointestinal fluids, and other fluids can seep through the tears H formed by the staples S, even after the staples S are fully formed. The tissue T being treated can also become inflamed due to the manipulations and deformations that can occur during stapling. Still further, staples, as well as other objects and materials implanted during stapling procedures, generally lack the same characteristics as tissue in which they are implanted. For example, staples and other objects and materials can lack the natural flexibility of the tissue in which they are implanted. A person skilled in the art will recognize that it is often desirable for tissue to maintain as much of its natural characteristics as possible after staples are disposed therein.

Accordingly, there remains a need for methods and devices for reinforcing a staple line.

SUMMARY

Methods for implanting a tissue reinforcement material onto tissue are provided. The method can include engaging tissue between a cartridge assembly and an anvil of a surgical stapler at a surgical site, at least one of the cartridge assembly and the anvil having a tissue reinforcement material retained thereon. The tissue reinforcement material can include a central region configured to provide a seal around a staple penetration site (e.g. in the tissue, in the central region, etc.) and an outer region adjacent to the central region and defining an edge of the tissue reinforcement material. Actuating the surgical stapler can eject staples from the cartridge assembly so as to form a staple line through the central region and into the tissue to hold the tissue reinforcement material at the surgical site. After actuating the surgical stapler, sealant can be delivered to the tissue reinforcement material when the sealant is in a first, liquid state such that the sealant solidifies thereon and reinforces a seal of the tissue at the staple line.

The method can vary in any number of ways. In certain aspects, actuating the surgical stapler ejects the staples through the central region of the tissue reinforcement material. The method can further include inserting the cartridge assembly and the anvil into the surgical site with the outer region of the tissue reinforcement material folded around at least one of the cartridge assembly and the anvil. Actuating the surgical stapler can release the tissue reinforcement material from the surgical stapler. In certain aspects, the surgical stapler advances the cutting member through the central region of the tissue reinforcement material. In other aspects, the surgical stapler forms a staple line having at least two rows of staples.

The sealant can be delivered to tissue in various ways. In certain aspects, the sealant is delivered through an applicator tool positioned adjacent to the tissue reinforcement material. Delivering the sealant can include depositing the sealant onto both the central and outer regions of the reinforcement material. In certain aspects, the sealant is delivered to the tissue reinforcement material in the first, liquid state, and the sealant penetrates a space in the tissue at the staple line and solidifies therein.

Systems for reinforcing a tissue seal are also provided. The system can include a sealant, a container, and an applicator tool. The sealant can be configured to transition from a first liquid state to a second solid state. The container can be configured to retain the sealant therein when the sealant is in the first liquid state, the container having a first port for receiving a gas and a second port for outputting nebulized sealant. The applicator tool can be coupled to the second port of the container, the applicator tool being configured to deliver the nebulized sealant to a surgical site.

The system can vary in any number of ways. In certain aspects, the applicator tool is a trocar. In other aspects, the gas includes carbon dioxide. In other aspects, the sealant includes a mixture of collagen, fibrinogen, and thrombin. These biologic materials may be derived from human and/or animal sources. The sealant can be configured to transition from the first liquid state to the second solid state after a predetermined amount of time. The system can include additional components. For example, a first tube can extend between the second port of the container and the applicator for receiving nebulized sealant.

Methods for delivering sealant to a body of a patient are also provided. The method can include delivering gas to a container having a sealant retained therein, thereby transitioning the sealant from a first, liquid state to a second, nebulized state. The nebulized sealant can be delivered through an applicator tool extending through an access port in a patient, the nebulized sealant solidifying onto tissue and forming a seal thereon.

The method can be performed in various ways. For example, the applicator tool can be positioned in a thoracic cavity of a patient prior to delivering the gas to the container. In certain aspects, the applicator tool includes a trocar, and nebulized sealant is delivered directly through the trocar and into the patient. The method can include positioning a distal end of the applicator tool adjacent to a staple line in the tissue prior to delivering the nebulized sealant to the tissue. In certain aspects, the hardened sealant is absorbed into the body after a predetermined passage of time.

BRIEF DESCRIPTION OF THE DRAWINGS

The invention will be more fully understood from the following detailed description taken in conjunction with the accompanying drawings, in which.

DETAILED DESCRIPTION

Figure 1:
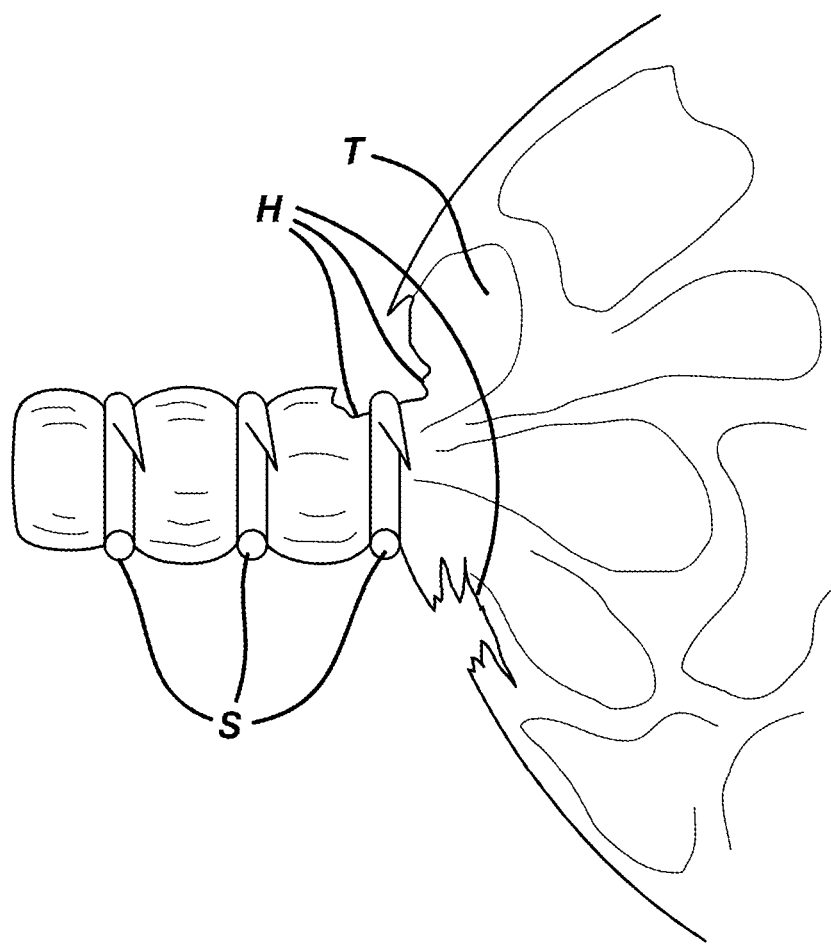
FIG. 1 is a side view of damaged stapled tissue.

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of such devices and methods is defined solely by the claims. The features illustrated or described in connection with one exemplary embodiment may be combined with the features of other embodiments. Such modifications and variations are intended to be included within the scope of the devices and methods described herein. Further, in the present disclosure, like-numbered components of the various embodiments generally have similar features when those components are of a similar nature and/or serve a similar purpose.

Reference throughout the specification to "various embodiments," "some embodiments," "one embodiment," or "an embodiment," or the like, means that a particular feature, structure, or characteristic described in connection with the embodiment is included in at least one embodiment. Thus, appearances of the phrases "in various embodiments," "in some embodiments," "in one embodiment," or "in an embodiment," or the like, in places throughout the specification are not necessarily all referring to the same embodiment. Furthermore, the particular features, structures, or characteristics may be combined in any suitable manner in one or more embodiments. Thus, the particular features, structures, or characteristics illustrated or described in connection with one embodiment may be combined, in whole or in part, with the features structures, or characteristics of one or more other embodiments without limitation. Such modifications and variations are intended to be included within the scope of the methods, apparatus, devices, and systems described herein.

The terms "proximal" and "distal" are used herein with reference to a clinician manipulating the handle portion of the surgical instrument. The term "proximal" referring to the portion closest to the clinician and the term "distal" referring to the portion located away from the clinician. It will be further appreciated that, for convenience and clarity, spatial terms such as "vertical," "horizontal," "up," and "down" may be used herein with respect to the drawings. However, surgical instruments are used in many orientations and positions, and these terms are not intended to be limiting and/or absolute.

It can be desirable to use one or more biologic materials and/or synthetic materials, collectively referred to herein as "adjunct materials," in conjunction with surgical instruments to help improve surgical procedures. These biologic materials may be derived from human and/or animal sources. A person skilled in the art may refer to these types of materials as buttress materials as well as adjunct materials.

Various exemplary devices and methods are provided for performing surgical procedures. In some embodiments, the devices and methods are provided for open surgical procedures, and in other embodiments, the devices and methods are provided for laparoscopic, endoscopic, and other minimally invasive surgical procedures. The devices may be fired directly by a human user or remotely under the direct control of a robot or similar manipulation tool. However, a person skilled in the art will appreciate that the various methods and devices disclosed herein can be used in numerous surgical procedures and applications. Those skilled in the art will further appreciate that the various instruments disclosed herein can be inserted into a body in any way, such as through a natural orifice, through an incision or puncture hole formed in tissue, or through an access device, such as a trocar cannula. For example, the working portions or end effector portions of the instruments can be inserted directly into a patient's body or can be inserted through an access device that has a working channel through which the end effector and elongated shaft of a surgical instrument can be advanced.

End effectors of the surgical instruments as described herein can be configured to deliver one or more synthetic materials and/or biologic materials, collectively referred to herein as "adjunct materials," to a surgical site to help improve surgical procedures. These biologic materials may be derived from human and/or animal sources. While a variety of different end effectors can benefit from the use of adjunct materials, in some exemplary embodiments the end effector can be a surgical stapler. When used in conjunction with a surgical stapler, the adjunct material(s) can be disposed between and/or on jaws of the stapler, incorporated into a staple cartridge disposed in the jaws, or otherwise placed in proximity to the staples. When staples are deployed, the adjunct material(s) can remain at the treatment site with the staples, in turn providing a number of benefits. In some instances, the adjunct material(s) can be used to help seal holes formed by staples as they are implanted into tissue, blood vessels, and various other objects or body parts, and/or can be used to provide tissue reinforcement at the treatment site. Tissue reinforcement may be needed to keep the staples from tearing through the tissue if the tissue is diseased, is healing from another treatment such as irradiation, medications such as chemotherapy, or other tissue property altering situation. In some instances, the adjunct material(s) may minimize tissue movement in and around the staple puncture sites that can occur from tissue deformation that occurs after stapling (e.g., lung inflation, gastrointestinal tract distension, etc.). It will be recognized by one skilled in the art that a staple puncture site may serve as a stress concentration and that the size of the hole created by the staple will grow when the tissue around it is placed under tension. Restricting the tissue's movement around these puncture sites can minimize the size the holes may grow to under tension. In some instances, the adjunct material(s) can be configured to wick or absorb beneficial fluids, e.g., sealants, blood, glues, that further promote healing, and in some instances, the adjunct material(s) can be configured to degrade to form a gel, e.g., a sealant, that further promotes healing. In some instances, the adjunct may carry materials that when placed into a wet environment (e.g., blood, water, saline, or other bodily fluids) form a sealant to create a seal (e.g., human or animal derived fibrinogen and thrombin can be lyophilized into a powder form that when mixed with water creates a sealant). Still further, the material(s) can help reduce inflammation, promote cell growth, and otherwise improve healing.

Figure 2:
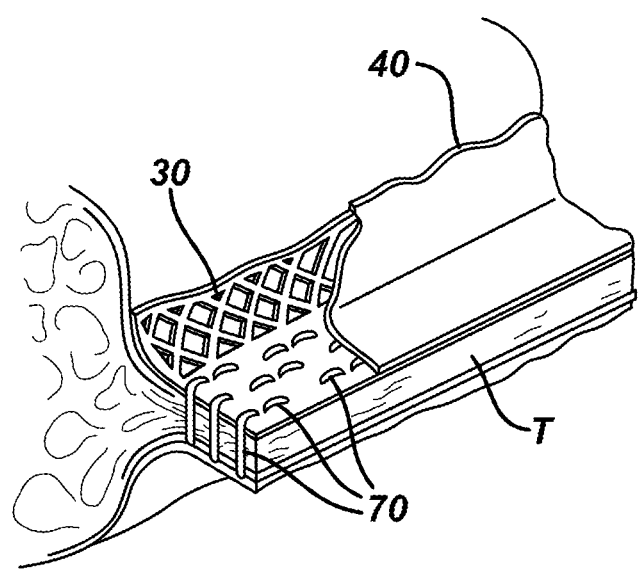
FIG. 2 is a perspective view of one embodiment of an adjunct material as described herein that is fixed to stapled tissue.

FIG. 2 illustrates one embodiment of an adjunct material that includes a porous buttress 30 that can be fixed to a tissue T to be treated by a surgical stapler and that remains at the treatment site with staples 70. The buttress 30 can be made from one or more absorbent materials and can be stamped, pressed, cut, molded, woven, melted, blown, comprised from composite structures and/or methods or otherwise shaped to facilitate absorption, reinforcement, delivery and/or retention of beneficial fluids such as sealants, glues, blood, etc. The absorption and/or retention of beneficial fluids, for example a fibrin sealant 40, at the treatment site can further help to prevent leaks and to reinforce the buttress 30.

Surgical Stapling Instrument

Figure 3:
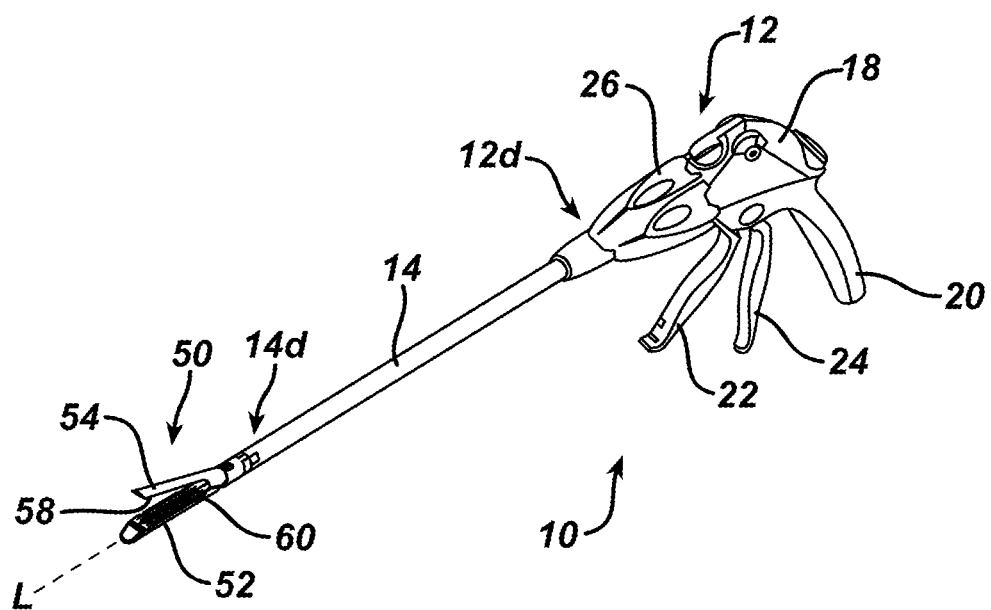
FIG. 3 is a perspective view of a prior art surgical instrument which can be used with one or more adjunct materials.

While a variety of surgical instruments can be used in conjunction with the adjunct materials disclosed herein, FIG. 3 illustrates one, non-limiting exemplary embodiment of a surgical stapler 10 suitable for use with one or more adjunct materials. The instrument 10 generally includes a handle assembly 12, a shaft 14 extending distally from a distal end 12d of the handle assembly 12, and an end effector 50 at a distal end 14d of the shaft 14. Because the illustrated embodiment is a surgical stapler, the end effector 50 has jaws 52, 54, although other types of end effectors can be used with the shaft 14, handle assembly 12, and components associated with the same. The surgical stapler 10 includes opposed lower and upper jaws 52, 54 with the lower jaw 52 including a staple channel 56 (FIG. 4) configured to support a staple cartridge 60, and the upper jaw 54 having an inner surface 58 that faces the lower jaw 52 and that is configured to operate as an anvil to help deploy staples 70 of the staple cartridge 60. The jaws 52, 54 are configured to move relative to one another to clamp tissue or other objects disposed therebetween, and components of a firing system can be configured to pass through at least a portion of the end effector 50 to eject the staples into the clamped tissue. In various embodiments a knife blade 81 can be associated with the firing system to cut tissue during the stapling procedure. At least one of the opposed lower and upper jaws 52, 54 will be moveable relative to the other lower and upper jaws 52, 54. At least one of the opposed lower and upper jaws 52, 54 may be fixed or otherwise immovable. In some embodiments, both of the opposed lower and upper jaws 52, 54 will be movable.

Operation of the end effector 50 can begin with input from a clinician at the handle assembly 12. The handle assembly 12 can have many different configurations designed to manipulate and operate the end effector 50 associated therewith. In the illustrated embodiment, the handle assembly 12 has a pistol-grip type housing 18 with a variety of mechanical and/or electrical components disposed therein to operate various features of the instrument. For example, the handle assembly 12 can include a rotation knob 26 mounted adjacent a distal end 12d thereof which can facilitate rotation of the shaft 14 and/or the end effector 50 with respect to the handle assembly 12 about a longitudinal axis L of the shaft 14. The handle assembly 12 can further include clamping components as part of a clamping system actuated by a clamping trigger 22 and firing components as part of the firing system that are actuated by a firing trigger 24. The clamping and firing triggers 22, 24 can be biased to an open position with respect to a stationary handle 20, for instance by a torsion spring. Movement of the clamping trigger 22 toward the stationary handle 20 can actuate the clamping system, described below, which can cause the jaws 52, 54 to collapse towards each other and to thereby clamp tissue therebetween. Movement of the firing trigger 24 can actuate the firing system, described below, which can cause the ejection of staples from a staple cartridge disposed therein and/or the advancement the knife blade 81 to sever tissue captured between the jaws 52, 54. A person skilled in the art will recognize that various configurations of components for a firing system, mechanical, hydraulic, pneumatic, electromechanical, robotic, or otherwise, can be used to eject staples and/or cut tissue, and thus a detailed explanation of the same is unnecessary.

Figure 4:
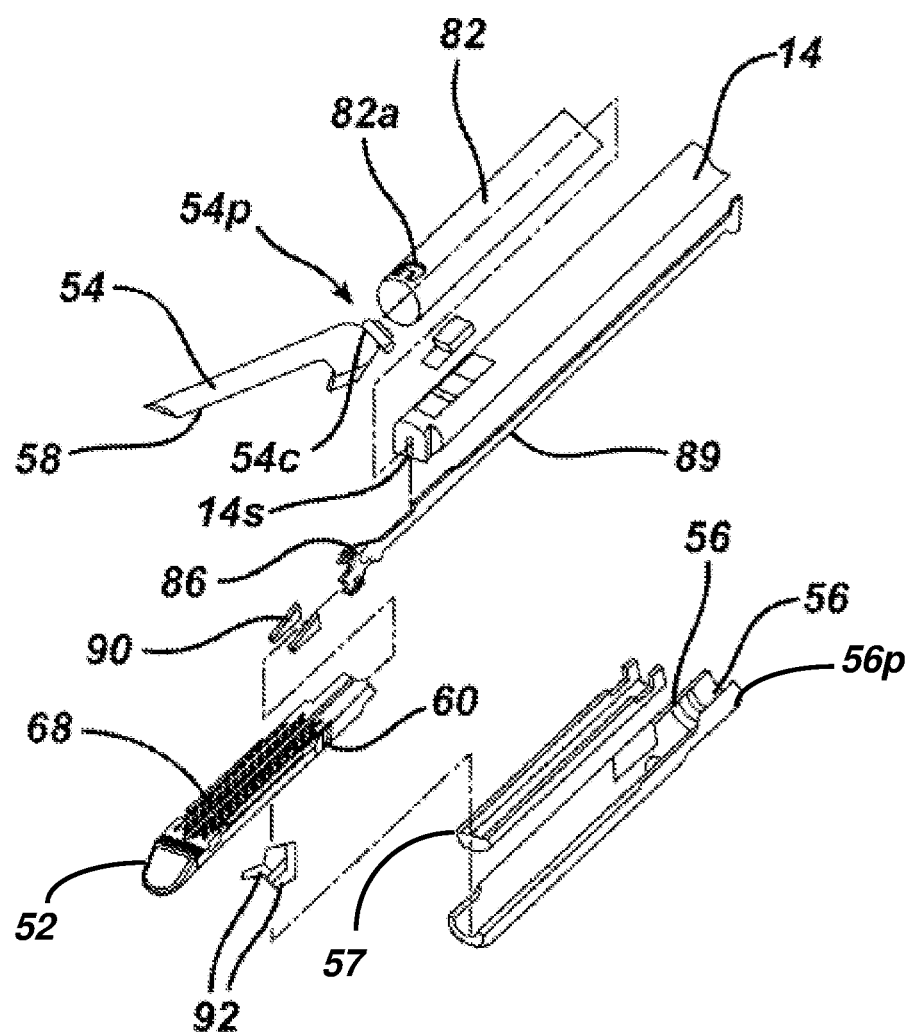
FIG. 4 is an exploded perspective view of an end effector and a distal end of a shaft of the instrument of FIG. 3.

As shown in more detail in FIG. 4, the end effector 50 of the illustrated embodiment is a surgical stapling tool having a lower jaw 52 that serves as a cartridge assembly or carrier and an opposed upper jaw 54 that serves as an anvil. The staple cartridge 60, having a plurality of staples 70 therein, is supported in a staple tray 57, which in turn is supported within the cartridge channel of the lower jaw 52. The upper jaw 54 has a plurality of staple forming pockets 366 (FIG. 11), each of which is positioned above a corresponding staple from the plurality of staples 370a, 370b contained within the staple cartridge 60. The upper jaw 54 can be connected to the lower jaw 52 in a variety of ways, although in the illustrated embodiment the upper jaw 54 has a proximal pivoting end 54p that is pivotally received within a proximal end 56p of the staple channel 56, just distal to its engagement to the shaft 14. When the upper jaw 54 is pivoted downwardly, the upper jaw 54 moves the anvil surface 58 and the staple forming pockets 366 formed thereon move toward the opposing staple cartridge 60.

Various clamping components can be used to effect opening and closing of the jaws 52, 54 to selectively clamp tissue therebetween. In the illustrated embodiment, the pivoting end 54p of the upper jaw 54 includes a closure feature 54c distal to its pivotal attachment with the staple channel 56. Thus, a closure tube 82, whose distal end includes a horseshoe aperture 82a that engages the closure feature 54c, selectively imparts an opening motion to the upper jaw 54 during proximal longitudinal motion and a closing motion to the upper jaw 54 during distal longitudinal motion of the closure tube 82 in response to the clamping trigger 22. It will be appreciated by a person skilled in the art that opening and closure of the end effector 50 may be effected by relative motion of the lower jaw 52 with respect to the upper jaw 54, relative motion of the upper jaw 54 with respect to the lower jaw 52, or by motion of both jaws 52, 54 with respect to one another.

Figure 5:
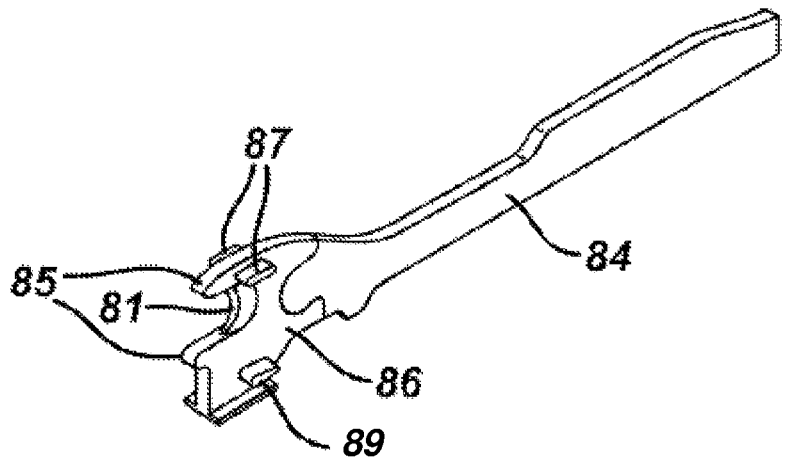
FIG. 5 is a perspective view of an E-beam component of the instrument of FIG. 3.

The firing components of the illustrated embodiment can include a firing bar 84, as shown in FIG. 5, having an E-beam 86 on a distal end thereof. The firing bar 84 is encompassed within the shaft 14, for example in a longitudinal firing bar slot 14s of the shaft 14, and guided by a firing motion from the handle 12. Actuation of the firing trigger 24 can affect distal motion of the E-beam 86 through at least a portion of the end effector 50 to thereby cause the firing of staples 70 contained within the staple cartridge 60. In the illustrated embodiment, guides 85 projecting from a distal end of the E-Beam 86 can engage a wedge sled 90, which in turn can push staple drivers 92 upwardly through staple cavities 68 formed in the staple cartridge 60. Upward movement of the staple drivers 92 applies an upward force on each of the plurality of staples 70 within the cartridge 60 to thereby push the staples 70 upwardly against the anvil surface 58 of the upper jaw 54 and to create formed staples 70'.

In addition to causing the firing of staples, the E-beam 86 can be configured to facilitate closure of the jaws 52, 54, spacing of the upper jaw 54 from the staple cartridge 60, and/or severing of tissue captured between the jaws 52, 54.

In particular, a pair of top pins 87 and a pair of bottom pins 89 can engage one or both of the upper and lower jaws 52, 54 to compress the jaws 52, 54 toward one another as the firing bar 84 advances through the end effector 50. Simultaneously, a knife 81 extending between the top and bottom pins 87, 89 can be configured to sever tissue captured between the jaws 52, 54.

In use, the surgical stapler 10 can be disposed in a cannula or port and disposed at a surgical site. A tissue to be cut and stapled can be placed between the jaws 52, 54 of the surgical stapler 10. Features of the stapler 10 can be maneuvered as desired by the clinician to achieve a desired location of the jaws 52, 54 at the surgical site and the tissue with respect to the jaws 52, 54. After appropriate positioning has been achieved, the clamping trigger 22 can be pulled toward the stationary handle 20 to actuate the clamping system. The trigger 22 can cause components of the clamping system to operate such that the closure tube 82 advances distally through at least a portion of the shaft 14 to cause at least one of the jaws 52, 54 to collapse towards the other to clamp the tissue disposed therebetween. Thereafter, the trigger 24 can be pulled toward the stationary handle 20 to cause components of the firing system to operate such that the firing bar 84 and/or the E-beam 86 are advanced distally through at least a portion of the end effector 50 to effect the firing of staples 70 and optionally to sever the tissue captured between the jaws 52, 54.

Figure 6:
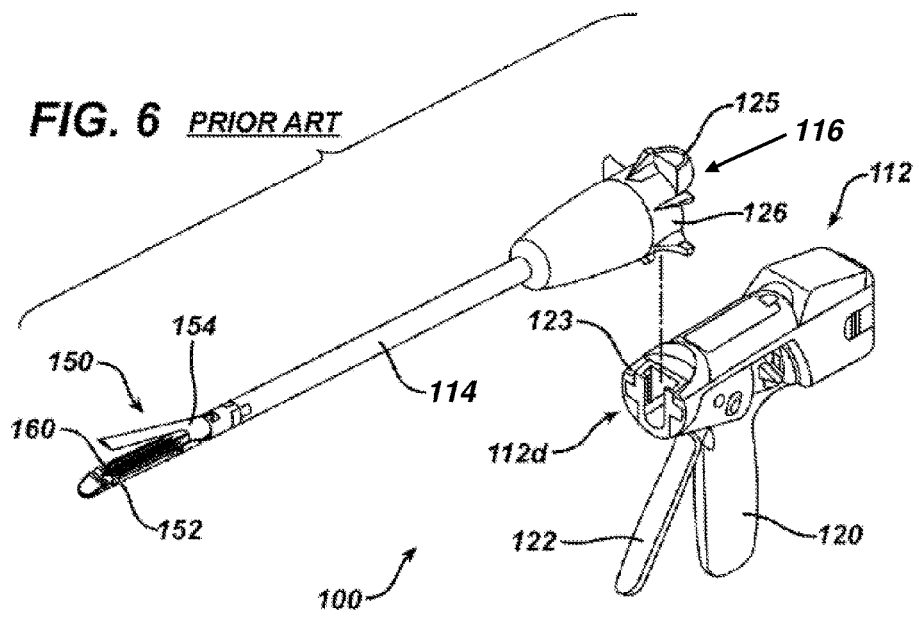
FIG. 6 is a perspective view of another prior art surgical instrument which can be used with one or more adjunct materials.

Another embodiment of a surgical instrument 100 is illustrated in FIG. 6. Like surgical instrument 10, surgical instrument 100 includes a handle assembly 112 with a shaft 114 extending distally therefrom and having an end effector 150 on a distal end thereof for treating tissue. Upper and lower jaws 154, 152 of the end effector 150 can be configured to capture tissue therebetween, staple the tissue by firing of staples from a cartridge 160 disposed in the lower jaw 154, and/or to create an incision in the tissue. In this embodiment, an attachment portion 116 on a proximal end of the shaft 114 can be configured to allow for removable attachment of the shaft 114 and the end effector 150 to the handle assembly 112. In particular, mating features 125 of the attachment portion 116 can mate to complementary mating features 123 at a distal end 112d of the handle assembly 112. The mating features 123, 125 can be configured to couple together via, e.g., a snap fit coupling, a bayonet type coupling, etc., although any number of complementary mating features and any type of coupling can be used to removably couple the shaft 114 to the handle assembly 112. Although the entire shaft 114 of the illustrated embodiment is configured to be detachable from the handle assembly 112, in some embodiments the attachment portion 116 can be configured to allow for detachment of only a distal portion of the shaft 114. Detachable coupling of the shaft 114 and/or the end effector 150 can allow for selective attachment of a desired end effector 150 for a particular procedure, and/or for reuse of the handle assembly 112 for multiple different procedures.

The handle assembly 112 can have one or more features thereon to manipulate and operate the end effector 150. By way of non-limiting example, a rotation knob 126 mounted on a distal end of the handle assembly 112 can facilitate rotation of the shaft 114 and/or the end effector 150 with respect to the handle assembly 112. The handle assembly 112 can further include clamping components as part of a clamping system actuated by trigger 122 and firing components as part of a firing system that can also be actuated by the trigger 122. Thus, in some embodiments, movement of the trigger 122 toward a stationary handle 120 through a first range of motion can actuate clamping components to cause opposed jaws 152, 154 to approximate toward one another to a closed position. Further movement of the trigger 122 toward the stationary handle 120 through a second range of motion can actuate firing components to cause the ejection of staples from the staple cartridge 160 and/or the advancement of a knife to sever tissue captured between the jaws 152, 154.

Figure 7:
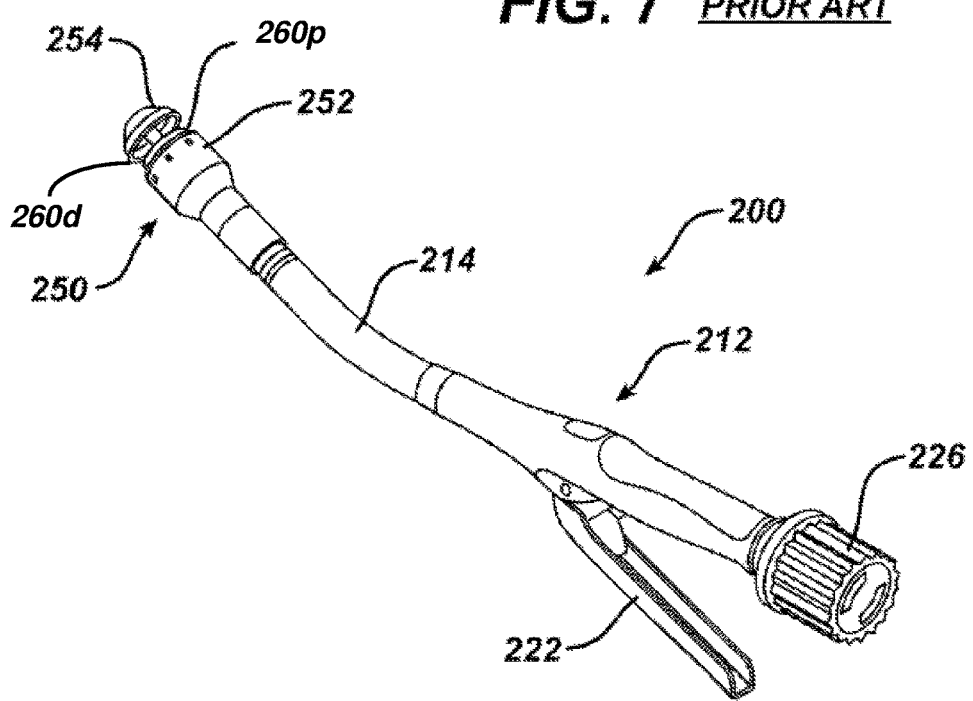
FIG. 7 is a perspective view of another prior art surgical instrument which can be used with one or more adjunct materials.

Yet another embodiment of a surgical instrument 200 is illustrated in FIG. 7. Like surgical instruments 10 and 100, surgical instrument 200 includes a handle assembly 212 with a shaft 214 extending distally therefrom and having an end effector 250 on a distal end thereof for treating tissue. The end effector 250 can include a cartridge assembly 252 and an anvil 254, each having a tissue-contacting surface 260p, 260d that is substantially circular in shape. The cartridge assembly 252 and anvil 254 can be coupled together via a shaft 262 extending from the anvil 254 to the handle assembly 212 of the stapler 200, and manipulating an actuator 222 on the handle assembly 212 can retract and advance the shaft 262 to move the anvil 254 relative to the cartridge assembly 252. In one embodiment, the shaft 262 can be formed of first and second portions (not shown) configured to releasably couple together to allow the anvil 254 to be detached from the cartridge assembly 252, allowing greater flexibility in positioning the anvil 254 and the cartridge assembly 252 in a body. For example, the first portion of the shaft can be disposed within the cartridge assembly 252 and extend distally outside of the cartridge assembly 252, terminating in a distal mating feature. The second portion of the shaft 214 can be disposed within the anvil 254 and extend proximally outside of the cartridge assembly 252, terminating in a proximal mating feature. In use, the proximal and distal mating features can be coupled together to allow the anvil 254 and cartridge assembly 252 to move relative to one another. The anvil 254 and cartridge assembly 252 can perform various functions and can be configured to capture tissue therebetween, staple the tissue by firing of staples from a cartridge assembly 252 and/or can create an incision in the tissue. In general, the cartridge assembly 252 can house a cartridge containing the staples and can deploy staples against the anvil 254 to form a circular pattern of staples around a circumference of a tubular body organ.

The handle assembly 212 of the stapler 200 can have various actuators disposed thereon that can control movement of the stapler. For example, the handle assembly 212 can have a rotation knob 226 disposed thereon to facilitate positioning of the end effector 250 via rotation, and/or a trigger 222 for actuation of the end effector 250. Movement of the trigger 222 through a first range of motion can actuate components of a clamping system to approximate the jaws, i.e. move the anvil 254 toward the cartridge assembly 252. Movement of the trigger 222 through a second range of motion can actuate components of a firing system to cause the staples to deploy from the staple cartridge assembly 252 and/or cause advancement of a knife to sever tissue captured between the cartridge assembly 252 and the anvil 254.

The illustrated embodiments of surgical stapling instruments 10, 100, and 200 provide only a few examples of many different configurations, and associated methods of use, that can be used in conjunction with the disclosures provided herein. Although the illustrated embodiments are all configured for use in minimally invasive procedures, it will be appreciated that instruments configured for use in open surgical procedures, e.g., open linear staplers as described in U.S. Pat. No. 8,317,070, can be used in conjunction with the disclosures provided herein. Greater detail on the illustrated embodiments, as well as additional exemplary embodiments of surgical staplers, components thereof, and their related methods of use, that can be used in accordance with the present disclosure include those devices, components, and methods provided for in U.S. Publication No. 2013/0256377, U.S. Pat. Nos. 8,393,514, 8,317,070, 7,143,925, U.S. patent application Ser. No. 14/074,884, entitled "Sealing Materials for Use in Surgical Procedures, and filed on Nov. 8, 2013, U.S. patent application Ser. No. 14/074,810, entitled "Hybrid Adjunct Materials for Use in Surgical Stapling," and filed on Nov. 8, 2013, U.S. patent application Ser. No. 14/075,438, entitled "Positively Charged Implantable Materials and Method of Forming the Same," and filed on Nov. 8, 2013, U.S. patent application Ser. No. 14/075,459, entitled "Tissue Ingrowth Materials and Method of Using the Same," and filed on Nov. 8, 2013, U.S. patent application Ser. No. 14/074,902, entitled "Hybrid Adjunct Materials for Use in Surgical Stapling," and filed on Nov. 8, 2013, U.S. patent application Ser. No. 14/226,142, entitled "Surgical Instrument Comprising a Sensor System," and filed on Mar. 26, 2014, each of which is incorporated by reference herein in its entirety.

End Effector Variations

End effectors of the surgical stapling instruments described herein can have one or more features for adjusting an amount of compression applied to tissue captured by the end effector. In some embodiments, the end effector can be configured to create a desired compression profile in tissue captured therein, for example a profile that helps to minimize bleeding, tearing, and/or leakage of the treated tissue. By way of non-limiting example, the desired tissue compression profile can be obtained using variations in a gap between upper and lower jaws of the end effector and/or variations in the orientation, size, and/or shape of staples applied to tissue by the end effector. As described in detail herein, adjunct material(s) used in conjunction with such an end effector can be configured to assist in creating the desired tissue compression profile and/or to accommodate features used to create the desired tissue compression profile.

Any such variations described herein can be used alone or together to provide the desired tissue compression profile. Although exemplary end effectors and components thereof are described in conjunction with a particular surgical instrument, e.g., instruments 10, 100, and 200, it will be appreciated that the end effectors and components thereof can be configured for use with other embodiments of surgical instruments as described herein.

Figure 8:
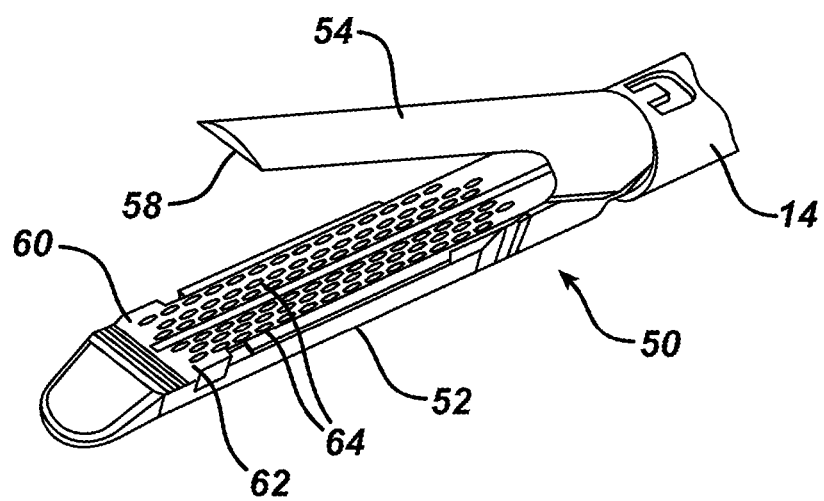
FIG. 8 is a perspective view of the end effector of FIG. 4.

In some embodiments, a staple cartridge disposed within an end effector of a surgical stapling instrument can have a first portion configured to compress tissue captured by the end effector more than a second portion when the end effector is in a closed position. The first portion of the cartridge can be spaced longitudinally and/or laterally from the second portion to create a desired compression gradient. For example, as shown in FIGS. 4 and 8, the staple cartridge 60 can have a stepped tissue contacting surface. In particular, the cartridge 60 can have an inner tissue contacting surface 62 and outer tissue contacting surfaces 64 that extend upwardly to a taller height than the inner tissue contacting surface 62. In this way, when the upper jaw 54 is in the closed position in close approximation with the cartridge 60, the anvil surface 58 can be configured to compress the outer surfaces 64 more than the inner surface 62 due to the taller height of the outer surfaces 64. In some circumstances, including circumstances where tissue positioned between the anvil surface 58 and the cartridge 60 has a constant, or at least substantially constant, thickness, the pressure generated within the tissue can be greater at outer portions of the end effector 50 than at inner portions of the end effector 50. Whereas a compression gradient generated by the cartridge 60 varies in a stepped manner, it will be appreciated by a person skilled in the art that a gradual compression gradient can be generated within the tissue by a gradual increase in height of various portions of the cartridge 60. It will also be appreciated that a compression gradient can be obtained by variations in height of the anvil surface 58, alone or in combination with height variations of the cartridge 60, and that height variations can be spaced laterally and/or longitudinally across the end effector 50.

Figure 9:
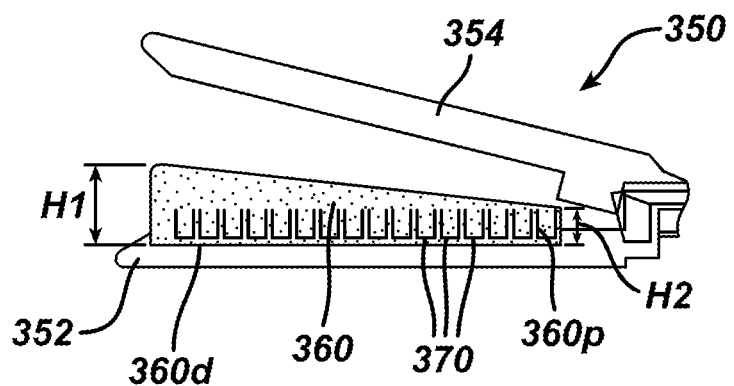
FIG. 9 is a side view of a prior art end effector having an implantable staple cartridge therein.

In some embodiments, one or more adjunct materials fixed to an end effector of a surgical stapling instrument can be used to create a desired compression profile in tissue captured by the end effector. Referring now to FIG. 9, a compressible, implantable staple cartridge 360 can be formed from one or more adjunct materials as described herein and can be configured to be seated within an end effector of a surgical instrument, e.g., an end effector 350. The cartridge 360 can have a height that decreases from a tallest height H1 at a distal end 360*d* thereof to a smallest height H2 at a proximal end 360*p* thereof. In this way, when an upper jaw 354 of the end effector 350 is in the closed position in close approximation with the cartridge 360, an upper jaw 354 of the end effector 350 can be configured to compress the distal end 360*d* more than the proximal end 360*p*. Although the compression gradient created in the captured tissue by the cartridge 360 decreases linearly from the distal end 360*d* to the proximal end 360*p*, it will appreciated by a person skilled in the art that any compression gradient can be created by different shapes of the cartridge 360. In at least one embodiment, a thickness of the cartridge 360 can vary across its width, similar to the cartridge 360.

Figure 10:
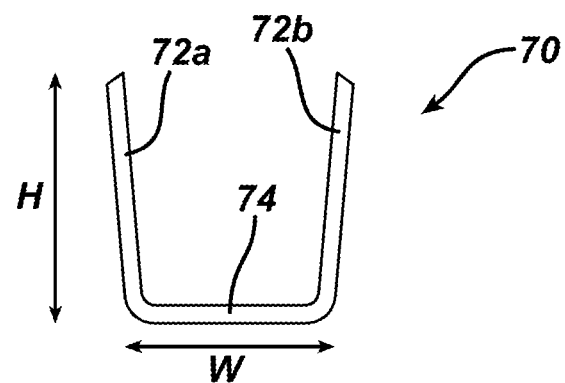
FIG. 10 is a side view of a prior art staple.
Figure 11:
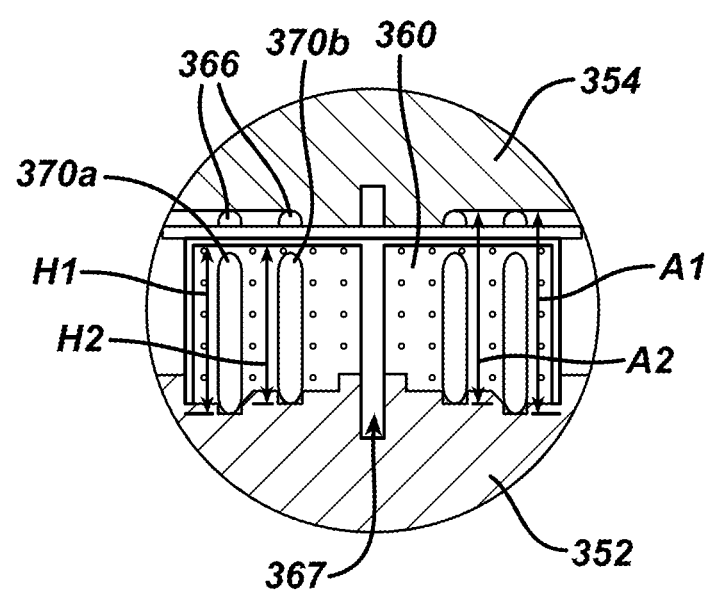
FIG. 11 is a cross-sectional view of the end effector of FIG. 9.

In some embodiments, staples contained within a staple cartridge of an end effector can be configured to create a desired compression profile within tissue captured by the staples. The desired compression profile can be created in stapled tissue, for example, where staples within the staple cartridge have different unformed staple heights. As shown in FIG. 10, an unformed height H of the exemplary staple 70 can be measured from a base 74 of the staple 70 to a top, or tip, of legs 72*a*, 72*b* of the staple 70. Referring now to FIG. 11, which illustrates a cross section of the end effector 350, a first group of staples 370*a* can have first staple height H1 that is taller than a second staple height H2 of a second group of staples 370*b*. The first group of the staples 370*a* can be positioned in a first portion of the staple cartridge 360, for example in an outer portion, and the second group of staples 370*b* can be positioned in a second portion of the staple cartridge 360, for example in an inner portion. In the illustrated embodiment, the cartridge 360, and therefore the compression gradient, can be configured to be symmetrical about a slot 367 configured to receive a cutting instrument, e.g., the E-beam 86, therethrough. It will be appreciated by a person skilled in the art that the first and second groups of staples 370*a*, 370*b* can be arranged in any pattern and can be spaced laterally and/or longitudinally along the cartridge 360. In certain embodiments, a plurality of staple groups, each group having different unformed staple heights, can be utilized. In at least one such embodiment, a third group having an intermediate staple height can be positioned in the cartridge intermediate the first group of staples and the second group of staples. In various embodiments, each staple within a staple row in the staple cartridge can comprise a different staple height. In at least one embodiment, the tallest staple within a staple row can be positioned on a first end of a staple row and the shortest staple can be positioned on an opposite end of the staple row. In at least one such embodiment, the staples positioned intermediate the tallest staple and the shortest staple can be arranged such that the staple heights descend between the tallest staple and the shortest staple, for example.

Figure 12:
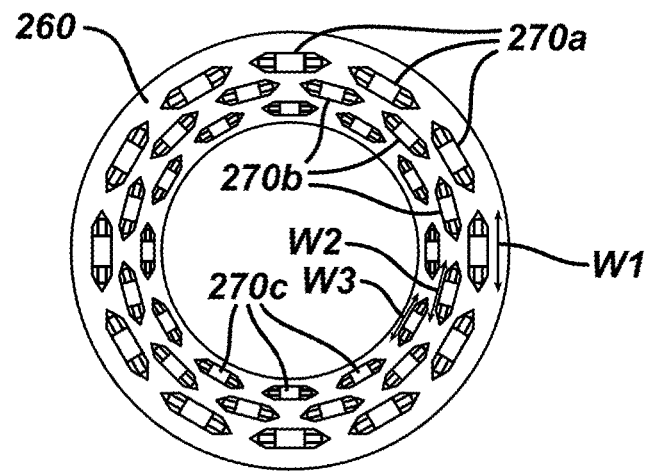
FIG. 12 is a top view of a prior art staple cartridge for use with the instrument of FIG. 7.

Similarly, staples within a staple cartridge can have different crown widths to create a desired compression profile in the stapled tissue. As shown in FIG. 10, a crown width W of the exemplary staple 70 can be measured from one side of the base 74 of the staple 70 to an opposite side. Like the above-described variations in staple height H, variations in the staple width W can be spaced throughout the staple cartridge to create a plurality of staple groups dispersed longitudinally and/or laterally across the cartridge. By way of non-limiting example, FIG. 12 illustrates a staple cartridge 260 for use with the surgical instrument 200 and having staples 270 therein with different crown widths W. The staple cartridge 260 houses three groups of staples 270*a*, 270*b*, 270*c*, each having different widths W1, W2, and W3, respectively, although any number of staple groups is possible. As shown, the groups of staples 270*a*, 270*b*, 270*c* can be arranged in circumferential rows, with the staples 270*c* having the largest width W1 positioned on an outermost edge of the cartridge 260 and the staples 270*a* having the smallest width W3 positioned on an innermost edge of the cartridge 260. In other embodiments, staples having a larger crown width can be positioned near an inner most edge of a cartridge and staples having a smaller crown width can be positioned near an outer edge of the cartridge. In still further embodiments, staples along the same row can have different crown widths.

Figure 13:
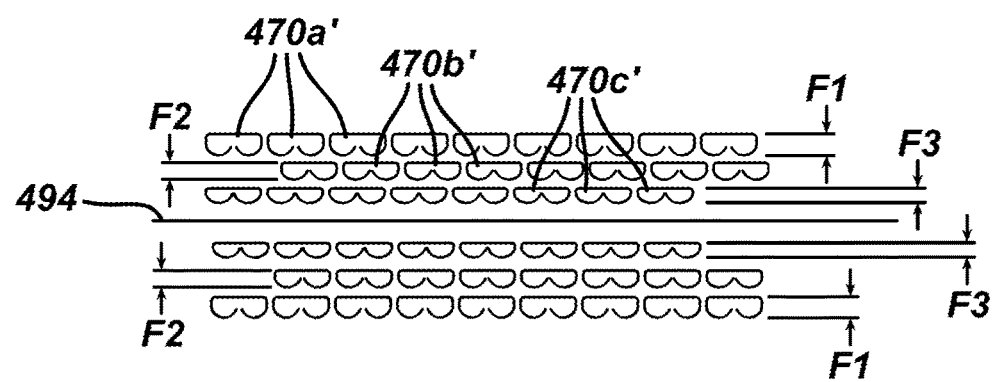
FIG. 13 is a diagrammatic representation of lines of staples installed using a prior art surgical stapling instrument.

Additionally or alternatively, it may be possible to create a desired tissue compression profile by the creation of different formed (final) staple heights. FIG. 13 illustrates an exemplary embodiment of lines of formed staples 470' installed using a surgical stapling instrument as described herein and configured to apply staples 470' having different formed heights as well as to cut tissue to thereby create a cut line 494. As shown in FIG. 13, formed heights F1 of a first group of staples 470*a*' in a first row that is the farthest distance away from the cut line 494 are greater than formed heights F3 of a third group of staples 470*c*' in a third row that is closest to the cut line 494. A second group of staples 470*b*' in a second row that is formed between the first and third rows can have staples 470*b*' with a formed height F2 that is between the heights F1, F3. In other embodiments, formed heights of the staples can decrease from an innermost row to an outermost row. In still further embodiments, formed heights of the staples in a single row can increase or decrease from staple to staple.

Referring again to FIG. 11, differences in formed staple heights can be attained by, for example, altering a staple forming distance A. Forming distances A1, A2 can be measured from a seat of staples 370*a*, 370*b*, respectively, within the cartridge 360, and an apex of a corresponding forming pocket 366 of the anvil surface 358 when the upper jaw 354 is in the closed position. In one embodiment, for example, a first staple forming distance A1 is different from a second staple forming distance A2. Because the forming distance A1 is greater than the forming distance A2, the staples 370*a* are not compressed as much as the staples 370*b*, which can alter the formed heights of the staples 370*a*, 370*b*. In particular, greater amounts of compression, corresponding to smaller forming distances, can result in staples with smaller formed (final) heights. It will be understood that similar results may be attained in any desired pattern.

Figure 14:
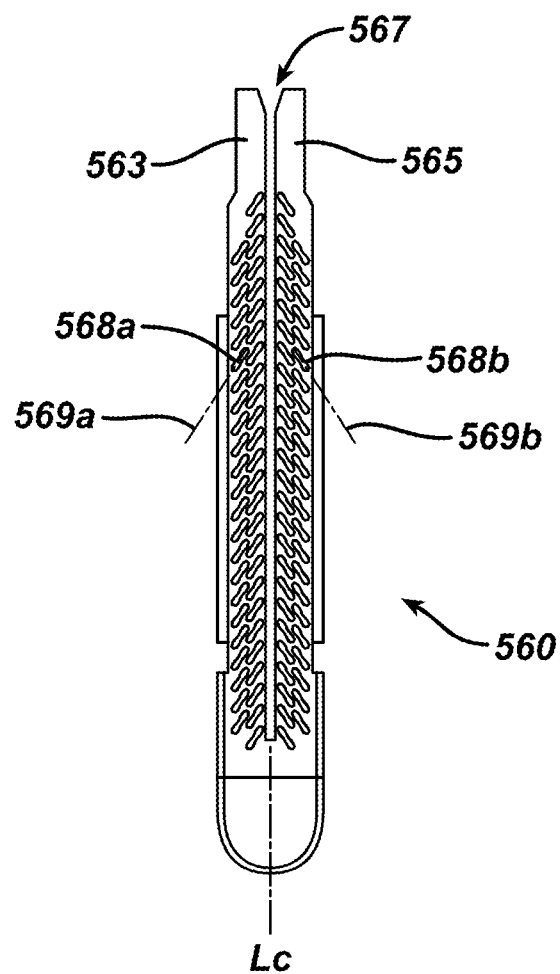
FIG. 14 is a top view of a prior art staple cartridge having a staple pattern.
Figure 15:
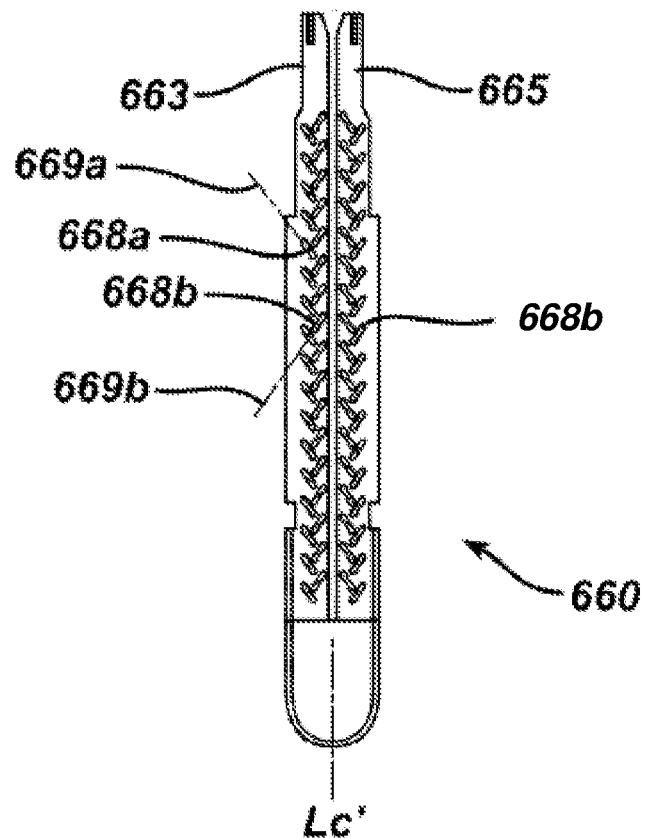
FIG. 15 is a side view of an end effector with a staple cartridge loaded with an adjunct material.

Varied tissue compression gradients can be obtained via patterns in staple orientation within a staple cartridge, for example by the patterns illustrated in FIGS. 14 and 15. In the embodiment depicted in FIG. 14, staple cartridge 560 can include at least one first staple cavity 568a and at least one second staple cavity 568b for housing staples 570 therein. The first cavity 568a can be situated on first lateral side 563 of the cartridge 560 and the second cavity 568b can be situated on a second lateral side 565 of the cartridge 560, the first and second lateral sides 563, 565 being separated by a slot 567 configured to receive a cutting instrument, e.g., the E-beam 86, therethrough. The first cavity 568a can define a first longitudinal axis 569a and the second cavity 568b can define a second longitudinal axis 569b. In the illustrated embodiment, the first axis 569a is perpendicular, or substantially perpendicular, to the second axis 569b. In other embodiments, the first axis 569a can be transverse to the second axis 569b such that axes 569a, 569b can create an acute or obtuse angle therebetween. In still other embodiments, the first axis 569a can be parallel to, or substantially parallel to, the second axis 569b. In some embodiments, at least a portion of the staple cavities 568a, 568b can overlap, such that staples 570 therein can be interlocked when formed. The cartridge 560 can have a plurality of each of the first and second cavities 568a, 568b, which can be arranged in any pattern on first and second sides 563, 565 of the cartridge 560, for example in rows extending along both sides 563, 565 of the cartridge 560 along a longitudinal axis Lc of the cartridge 560. The staples 570 housed within the cavities 568a, 568b can be implanted into tissue in a pattern determined by the orientation and positioning of the cavities 568a, 568b. The cartridge 560, for example, can be used to implant staples 570 having different orientations of the staples 570 on opposite sides of an incision line created by a surgical instrument carrying the cartridge 560.

In other embodiments, for example the embodiment of a cartridge 660 illustrated in FIG. 15, staple cavities 668a and 668b having different orientations can both be disposed on a single lateral side of the cartridge 660. As shown in FIG. 15, an axis 669a of the first staple cavity 668a is perpendicular, or substantially perpendicular, to an axis 669b of the second staple cavity 668b, both of which are disposed on each of first and second lateral sides 663, 665 of the cartridge 660. In other embodiments, the axes 669a, 669b can form an acute or obtuse angle therebetween, or can be parallel to one another. A plurality of the first and second cavities 668a, 668b can be aligned in adjacent rows along a longitudinal axis Lc' of the cartridge 660 on each of the first and second sides 663, 665 of the cartridge 660. In this embodiment, staples 670 housed within the cavities 668a, 668b can be implanted into tissue in a symmetrical pattern about an incision line created by a surgical instrument carrying the cartridge 660. Greater detail on staple patterns, as well as additional embodiments of such patterns, can be found in U.S. Publication No. 2011/0192882, incorporated herein by reference in its entirety.

Exemplary Compositions for Adjunct Materials

Figure 16:
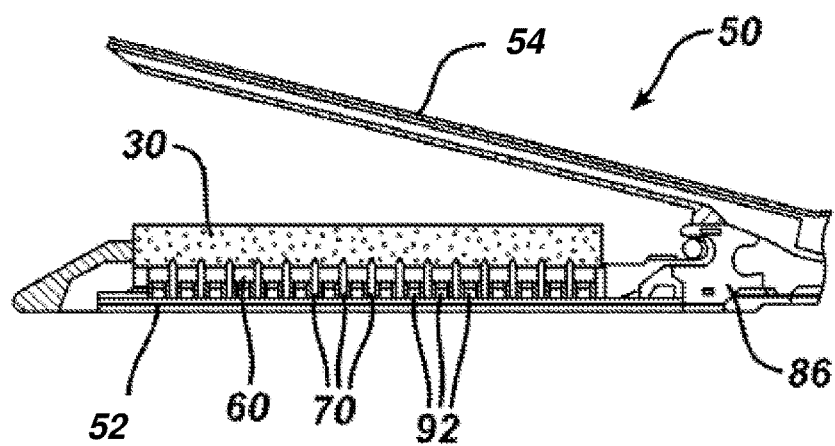
FIG. 16 is a side, cross-sectional view of the end effector of FIG. 4 having an adjunct material thereon.

Regardless of the configuration of the surgical instrument, the present disclosure provides for the use of implantable materials, e.g., synthetic and/or biological materials, collectively "adjunct materials," in conjunction with instrument operations. As shown in FIG. 16, the end effector 50 can include at least one piece of adjunct material 30 positioned intermediate the lower and upper jaw members 52, 54 and it can be releasably retained to one of the staple channel 56 and/or the anvil surface 58. In use, the adjunct material 30 and patient tissue can be captured by staples 70 when the staples 70 are fired. Then, the adjunct material 30 can be separated from the surgical stapler and can remain in the patient when the stapler is removed from the patient. Exemplary devices and methods for attaching one or more adjunct materials to an end effector of a surgical instrument can be found in U.S. Publication No. 2013/0256377 and U.S. Publication No. 2013/0153641, incorporated herein by reference in their entirety.

Adjunct material used in conjunction with the disclosures provided for herein can have any number of configurations and properties. Generally, they can be made from a bioabsorbable material, a biofragmentable material, and/or a material otherwise capable of being broken down, for example, such that the adjunct material can be absorbed, dissolved, fragmented, and/or broken down during the healing process. In at least one embodiment, the adjunct material can be configured to degrade over time to form a gel, e.g., a sealant, to assist in wound healing. In other embodiments, the adjunct material can include a therapeutic drug that can be configured to be released over time to aid the tissue in healing, for example. In further various embodiments, the adjunct materials can include a non-absorbable and/or a material not capable of being broken down, for example.

Some particularly advantageous adjunct materials can include porous polymer scaffolds that can be configured to be broken down, for example by exposure to water such that the water attacks the linkage of a polymer of the material. The degraded material can be configured to gel over a wound site to thereby coat the wounded tissue, e.g., wounded soft tissue, which can aid in compressing, sealing and/or generally creating an environment at the wound site that promotes healing of the tissue. In particular, such degradable polymers can allow for the tissue itself to become the weight-bearing component. In some embodiments, the degraded material can include chemoattractant agents that attract natural healing compounds to the wound site. The polymer scaffolds can be configured to have a desired rate of degradation, for example within minutes to hours after attachment to tissue, to thereby assist in the healing process almost immediately after attachment. For more details on porous polymer scaffolds as described herein, see Q. Chen et al., Elastomeric biomaterials for tissue engineering, Progress in Polymer Science 38 (2013) 584-671, incorporated herein by reference in its entirety.

In some embodiments, the porous polymer scaffolds described herein can be physically crosslinked, which can allow for shaping of the polymer into various complicated three-dimensional shapes, e.g., fibers, sheets, films etc., having any desired porosity, surface-to-volume ratio, and mechanical properties. The scaffold can be shaped into a desired form via a number of methods, for example by extrusion, wet spinning, electrospinning, thermally induced phase separation (TIPS), salt leaching/freeze-drying, etc. Where the scaffold is formed into a film or sheet, the film or sheet can have any desired thickness, for example in a range of about 50 to 750 µm or in a range of about 1 to 3 mm, depending on the desired application.

One embodiment of a porous polymer scaffold includes multiple layers, each of which can perform different wound healing functions. In an exemplary embodiment, the scaffold includes three layers. The first layer can be made from polyester carbonate urethane urea (PECUU), the second layer can be made from poly(ester urethane) urea (PEUU), and the third layer can be made from poly(carbonate urethane) urea (PCUU) lysine triisocyanate (LTI) or hexamethylene diisocyanate (HDI). A person skilled in the art will appreciate that the properties of each layer can be optimized to achieve desired results and performance. In some embodiments, the desired properties of the scaffold can be achieved by blending or copolymerizing the material of the third layer or copolymerized with various polymers or copolymers. By way of non-limiting examples, the material of the third layer can be blended with a polyester copolymer, for example polycaprolactone (PCL), polyglycolic acid PGA, poly(D,L-lactic acid) (PDLLA), PGA, and/or polyethylene glycol (PEG). Where the material of the third layer is blended with both the polyester copolymer and the PEG, a ratio of the polyester to the PEG in the third layer can be about 50:50. In another exemplary embodiment, the PCL can be present in a range of about 60-70% weight/volume, the PGA can be present in a range of about 20-30% weight/volume, the PEG can be present in a range of about 50% weight/volume, and the PDLLA can be present in a range of about 10% weight/volume.

The three-layered film can be configured to degrade almost immediately upon attachment to tissue, for example within about 1 to 2 hours after attachment, although each of the three layers can be configured to degrade differently to have different healing benefits. The order, number, and thickness of each of the layers can vary, and can be tailored to create desired degradation and/or compression ratios. In some embodiments, the first, second, and third layers can be formed on top of a base material or substrate, for example on top of PCL, which can be configured to aid in mechanical compression of the wounded tissue.

Another exemplary embodiment of a porous polymer scaffold can be synthesized from polyhydroxyalkanoate (PHA). In an exemplary embodiment, the PHA can be naturally produced from a variety of microorganisms, e.g., Gram-negative or Gram-positive bacteria, or it can be synthesized, e.g., similar to the production of Biopol®, available from Zeneca of London, United Kingdom. Because PHAs are very quick to dissolve, scaffolds made from PHA can begin to degrade within 20 to 30 minutes after attachment to tissue via contact with heat and/or water. Where the PHA scaffold has a higher molecular weight, the degradation time can be higher, for example in a range of about 30 minutes to about 10 hours. The PHA can be formed into a very thin film, for example a film having a thickness of less than 0.1 mm, e.g., in a range of between 50 to 750 µm. In some embodiments, the PHA can be copolymerized and/or blended with one or more additional materials. By way of non-limiting example, the PHA can be copolymerized with hydroxlvalerate (HV), hydroxylbutyrate (HB), and/or hydroxylhexanoate (HH), which can reduce a level or crystallinity and/or brittleness of the PHA. In other embodiments, the PHA can be blended with one or more thermoplastics, e.g., poly(lactic acid) (PLA), PGA, PCL, starch, etc., to thereby customize a molecular weight and resultant mechanical properties of the scaffold. In certain aspects, one or more of the polymers can be a thermoplastic polymer.

In other embodiments, the scaffold can be synthesized from poly(polyol sebacate) (PPS), e.g., from poly(glycerol-sebacate) (PGS). Such scaffolds can be particularly biocompatible and can provide an additional advantage of reducing a risk of infection in addition to promoting healing. Other exemplary embodiments can be synthesized from xylitol-based elastomers, for example polyxylitol sebacates (PXSs), which can offer structural stability over a clinically required period and/or can enter the metabolic pathway slowly without causing rapid fluctuations of blood glucose levels. Scaffolds made from PXS's can be formed into a thicker film to thereby provide greater compression to the wound site, and can be configured to degrade within a range of about 10 hours to 8 days after attachment. Still other exemplary embodiments can be synthesized from poly(glycerol sebacate-co-acrylate) (PGSA), which can promote tissue ingrowth into the scaffold, particularly when formed as a fiber, and/or can serve as an antibacterial agent. PGSA scaffolds can be useful as a replacement for traditional surgical sutures and staples, and/or can serve as a waterproof sealant for hollow organ anastomoses (e.g., ducts, intestine, etc.), 2D mesh grafts (e.g., treatment of hernias, ulcers, burns, etc.), and/or wound dressings (e.g., hemostatic patches, etc.). The PGSA can be combined with glycerol, which can allow the scaffold to last longer in situ, for example up to 20 days.

In yet another embodiment, the scaffold can be made from poly(ε-caprolactone) (PCL), which can be blended with silk fibroin (SF) and which can be formed into a very thin film. The PCL/SF blend can have highly biocompatible properties and/or can improve cell attachment and/or proliferation to the scaffold. For example, when implanted onto tissue, the scaffold can release fibroin into the tissue to thereby promote faster healing, nearly immediate hemostasis, and/or to attract fibroblasts in greater numbers. The PCL component can further assist in the healing process by providing mechanical compression of the wounded tissue. A higher PCL content can provide better mechanical properties, while a higher SF content can provide better degradation properties. In general, the PCL content can be in a range of about 50 to 90% weight/volume and the SF content can be in a range of about 10 to 50% weight/volume. More details on the properties and manufacturing methods for scaffolds made from PCL and SF can be found in Jun Sik Lim et al., Fabrication and Evaluation of Poly(epsilon-caprolactone)/Silk Fibroin Blend Nanofibrous Scaffold, Biopolymers 97: 265-275 (2012), incorporated herein by reference in its entirety.

In still further embodiments, the scaffold can include PCL coated with a gelatin. The scaffold can be arranged in one or more layers, for example with the PCL serving as a substrate. The PCL can function to increase a mechanical strength of the scaffold and/or can support fibroblast adhesion and cell proliferation. More details on the properties and manufacturing methods for scaffolds made from gelatin-coated PCL can be found in Pengcheng Zhao et al., Biodegradable fibrous scaffolds composed of gelatin coated poly(ε-caprolactone) prepared by coaxial electrospinning, J. Biomed Mater Res 83A: 372-382 (2007), incorporated herein by reference in its entirety.

Table 1 below outlines exemplary molecular weight ranges, approximate absorption times, and average dimensions of films made from the aforementioned porous polymer scaffold materials. It will be appreciated by a person skilled in the art that the ranges provided in Table 1 are not intended to be limiting, and that a molecular weight of any of the polymers described herein can be altered to obtain the desired degradation properties.

TABLE 1

| Film | Average molecular weight in Daltons | Approximate absorption times | Average thickness | Average length | Average width |
|---|---|---|---|---|---|
| Polyester carbonate urethane urea (PECUU) | 5,000 to 80,000 | 14 to 60 days | 10 μm to 1 mil | 25.4 to 100 mm | 10.3 to 12.7 mm |
| Poly(ester urethane)urea (PEUU) | 5,000 to 80,000 | 14 to 60 days | 10 μm to 1 mil | 25.4 to 100 mm | 10.3 to 12.7 mm |
| Poly(carbonate urethane)urea (PCUU) | 10,000 to 200,000 (preferably 15,000 to 50,000) | 14 to 60 days | 100 μm to 1 mil | 25.4 to 100 mm | 10.3 to 12.7 mm |
| Polyhydroxyalkanoate (PHA) | $2.107 \times 10^{29}$ to $2.589 \times 10^{29}$ | 7 to 60 days | 100 μm to 1 mil | 25.4 to 100 mm | 10.3 to 12.7 mm |
| Poly(polyol sebacate) (PPS) | 89,000 and 124,000 | 7 to 60 days | 100 μm to 1 mil | 25.4 to 100 mm | 10.3 to 12.7 mm |
| Polyxylitol sebacates (PXS's) | $1.47 \times 10^{27}$ to $3.73 \times 10^{27}$ | 7 to 60 days | 100 μm to 1 mil | 25.4 to 100 mm | 10.3 to 12.7 mm |
| Poly(glycerol sebacate-co-acrylate) (PGSA) | $5.8 \times 10^{26}$ to $7.5 \times 10^{26}$ | 7 to 60 days | 10 μm to 1 mil | 25.4 to 100 mm | 10.3 to 12.7 mm |
| Poly(ε-caprolactone); silk fibroin; scaffold (PCL/SF) Blend PCL/SF (50/50) | 25,000 to 325,000 (SF) $4.21 \times 10^{28}$ to $4.81 \times 10^{28}$ (PCL) | 21 to 60 days (SF) 2 to 3 years (PCL) | 10 μm to 1 mil | 25.4 to 100 mm | 10.3 to 12.7 mm |
| Gelatin coated PCL (poly (ε-caprolactone) | $3.01 \times 10^{28}$ to $1.98 \times 10^{29}$ (gelatin) $4.21 \times 10^{28}$ to $4.81 \times 10^{28}$ (PCL) | 7 days (gelatin) 2 to 3 years (PCL) | 100 μm to 1 mil | 25.4 to 100 mm | 10.3 to 12.7 mm |

Other suitable adjunct materials can include absorbable polyurethanes, e.g., polyurethanes derived from aromatic absorbable isocyanates that can be similar to methylene bis(phenyl isocyanate) (MDI) and chain extender diols. The absorbable polyurethanes can be configured to hydrolytically degrade into safe and biocompatible products upon hydrolysis. Non-limiting examples of hydrolysable aromatic isocyanates that can be used to form the absorbable polyurethanes include glycolate-diisocyante, caprolactone-diisocyanate, glycolate-ethylene glycol-glycolate, glycolate-diethylene glycol-glycolate, lactate-diethylene glycol-lactate, trimester of gycolic acid with trimethylpropane, and tetraester of glycolic acid with pentaerythritol.

Another particularly advantageous adjunct material that can be used in conjunction with the disclosures provided herein are the materials that form the multilayered dressings disclosed in U.S. Publication No. 2006/0257458, incorporated herein in its entirety, which are particularly suited to absorb and retain fluids when compressed, e.g., by the application of staples. Other exemplary, non-limiting examples of synthetic materials that can be used in conjunction with the disclosures provided for herein, e.g., as a buttress, include biodegradable synthetic absorbable polymer such as a polydioxanon film sold under the trademark PDS® or with a Polyglycerol sebacate (PGS) film or other biodegradable films formed from PGA (Polyglycolic acid and various forms thereof, marketed under the trademarks Vicryl, Dexon, and/or Neoveil), PCL (Polycaprolactone), PLA or PLLA (Polylactic acid), PHA (polyhydroxyalkanoate), PGCL (poliglecaprone 25, sold under the trademark Monocryl), PANACRYL (Ethicon, Inc., Somerville, N.J.), Polyglactin 910, Poly glyconate, PGA/TMC (polyglycolide-trimethylene carbonate sold under the trademark Biosyn), polyhydroxybutyrate (PHB), poly(vinylpyrrolidone) (PVP), poly(vinyl alcohol) (PVA), polydioxanone (PDO) and various forms thereof (e.g., marketed under the trademark PDS) or a blend or copolymerization of any of the above. Blends and/or copolymerizations of any of the aforementioned materials can be tailored to have a desired molecular weight and/or degradation rate.

Some non-limiting examples of biologic derived materials that can be used in conjunction with the disclosures provided for herein, e.g., as a sealant material, include platelet poor plasma (PPP), platelet rich plasma (PRP), starch, chitosan, alginate, fibrin, thrombin, polysaccharide, cellulose, collagen, bovine collagen, bovine pericardium, gelatin-resorcin-formalin adhesive, oxidized regenerated cellulose, regenerated cellulose, mussel-based adhesive, poly (amino acid), agarose, polyetheretherketones, amylose, hyaluronan, hyaluronic acid, whey protein, cellulose gum, starch, gelatin, silk, Progel®, available from Davol Inc. of Warwick, R.I., TachoSil®, available from Baxter of Deerfield, Ill., or other material suitable to be mixed with biological material and introduced to a wound or defect site, including combinations of materials, or any material apparent to those skilled in the art in view of the disclosures provided for herein. Biologic materials can be derived from a number of sources, including from the patient in which the biologic material is to be implanted, a person that is not the patient in which the biologic material is to be implanted, or other animals.

Additional disclosures pertaining to synthetic or polymer materials and biologic materials that can be used in conjunction with the disclosures provided herein can be found in U.S. Pat. No. 7,772,352, PCT Publication No. WO 2014/016819, U.S. Patent Application Publication No. 2006/0257458, U.S. Patent Application Publication No. 2012/0080335, U.S. Patent Application Publication No. 2012/0083835, U.S. Patent Application Publication No. 2013/0256372, U.S. Patent Application Publication No. 2013/0256365, U.S. Patent Application Publication No. 2013/0256376, U.S. patent application Ser. No. 13/710,931, entitled "Electrosurgical End Effector with Tissue Tacking Features," and filed on Dec. 11, 2012, and U.S. patent application Ser. No. 13/763,192, entitled "Multiple Thickness Implantable Layers for Surgical Stapling Devices," and filed on Feb. 8, 2013, each of which is incorporated by reference herein in its entirety.

Adjuncts Having Strain Relieving Features

A tissue adjunct can have various configurations, but can generally be configured to contact tissue as the tissue is clamped between a cartridge assembly and an anvil of a surgical stapler. One advantage of tissue adjuncts is their propensity to prevent or minimize leaks, such as fluid or gas leaks. Tissue adjuncts can perform this function by one or more of the following mechanisms: plugging holes or tears that occur at the staple puncture sites; restricting movement of tissue around staple puncture sites to prevent an increase in the size of staple holes and/or to prevent tissue tears; and minimizing strain gradients that occur between constrained tissues within the staple line and free tissue adjacent to the staple line.

In certain aspects, the adjunct material can be used to distribute the compressive clamping force over the tissue, absorb and retain beneficial fluids at the treatment site, improve the purchase of the staples, and/or promote hemostasis. In some embodiments, a first piece of adjunct material can be attached to a cartridge assembly and a second piece of adjunct material can be attached to an anvil; however, any suitable number of adjunct materials can be situated within the end effector.

The tissue adjunct can include various features and be formed from various materials for assisting with sealing of tissue at a staple line and/or for preventing the formation of leaks in the tissue. For example, a tissue adjunct can have a central region configured to be deployed onto tissue and attached thereto via staples. The tissue adjunct can further include an outer region, also referred to herein as a wing region or wing portion, which can be positioned outside of a staple line when the adjunct is stapled to tissue. The wing portion can help to more evenly distribute strain and/or minimize strain gradients across a tissue as the tissue deforms or otherwise expands and contracts during normal bodily functions. In some embodiments, a sealant can be used in conjunction with the adjunct to help seal the stapled tissue. The sealant can be introduced into a patient in a first, liquid state and can be configured to transition to a second, hardened or solid state after a predetermined amount of time. When the sealant is in the first, liquid state, the sealant can seep into the adjunct and/or the staple line and then harden therein, thereby facilitating complete sealing of the tissue. The adjunct and the sealant can thus cooperate to provide a better, more complete seal of the staple line than if only the tissue adjunct or the sealant were used.

Figure 17A:
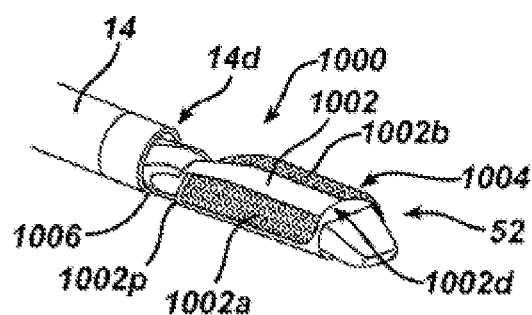
FIG. 17A is a perspective view of adjunct material having a central portion and a wing portion, the adjunct material being coupled to a cartridge assembly.
Figure 17B:
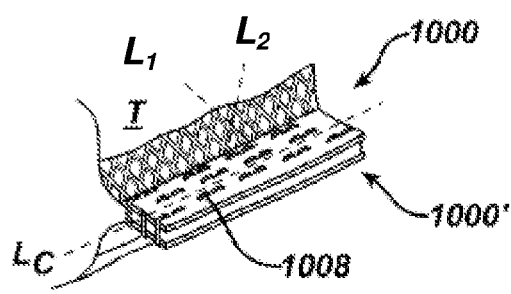
FIG. 17B is a perspective view of an adjunct material stapled onto tissue.

Exemplary adjuncts having central and wing regions are shown deployed onto tissue in FIGS. 17A and 17B. As shown in FIG. 17A, an adjunct 1000 can include a central region 1002 for receiving staples therethrough and a wing portion 1004 adjacent to the central region 1002. The central region 1002 of the adjunct 1000 can be sized and shaped to correspond to a size and shape of a cartridge assembly 52 and/or an anvil (not shown). For example, FIG. 17A illustrates an adjunct 1000 having a central region 1002 that corresponds in size and shape to a tissue-contacting surface of the cartridge assembly 52. That is, the central region 1002 can be substantially equal in size to the tissue-contacting surface. The central region 1002 of the adjunct 1000 shown in FIG. 17A can have a substantially elongate rectangular shape defined by proximal and distal edges 1002*p*, 1002*d* and first and second lateral edges 1002*a*, 1002*b*. The proximal edge 1002*p* of the central region 1002 can terminate in a proximal mating feature 1006 for coupling to a distal end 14*d* of a shaft 14 of a stapler 10. At least two of the remaining three edges of the central region 1002 can include a wing portion 1004 extending therearound and forming a perimeter of the adjunct 1000. For example, as shown in FIG. 17A, the wing portion 1004 of the adjunct 1000 can extend around the first and second lateral edges 1002*a*, 1002*b* and can extend distally beyond the distal edge 1002*d* of the central region 1002. In one embodiment, adjunct 1000 is sized and position in such a way on cartridge assembly 52 so that in can be separated by a cutting member in the stapler during use. In fact, a distal region of the wing portion 1004 is always cut. As shown, the wing portion 1004 can have a modified structure that is different from a structure of the central region 1002. In the illustrated embodiment, the central region 1002 can be substantially solid, e.g. a film, and the wing portion 1004 can be a mesh. As shown in FIG. 17B, when the adjunct 1000 is stapled to tissue T, the central region 1002 can have one or more rows/lines of staples 1008 extending therethrough and the wing portion 1004 can extend laterally away from the staples 1008. As shown, the adjunct 1000 stapled to the tissue T includes half of the adjunct shown in FIG. 17A because the cutting member in the stapler severs the tissue while the staples 1008 are deployed thereon. The meshed wing portion 1004 can flex as the tissue expands and contracts and more evenly distribute a strain (or minimize a strain gradient) across a greater area of tissue than if the adjunct 1000 only included the central region 1002. For example, the wing portion 1004 can expand and contract in a direction transverse to the longitudinal axis LC of the central region 1002. This can help prevent the formation of pressure points which can create leaks in the stapled tissue after repeated expansion and contraction of the tissue. In certain aspects, the mesh can be formed from threads of the same film material as the central region 1002 extending in a criss-cross pattern. The longitudinal axis of half of the threads L1 can be disposed at an angle θ1 of about a 45 degrees relative to the longitudinal axis LC of the central region 1002, as shown, and a longitudinal axis L2 of the other half of the threads can be disposed at an angle θ2 of about a 45 degree angle relative to the longitudinal axis LC of the central region 1002, or can be positioned at other angles relative to the central region 1002. As will be appreciated by a person skilled in the art, the wing portion 1004 of the adjunct 1000 can be formed using various known manufacturing techniques, such as laser cutting or punching shapes such as squares, circles, diamonds, out of the film to produce a mesh wing region and the solid central region 1002. Two identical adjuncts 1000, 1000' can be stapled to tissue, as shown in FIG. 17B, and in certain aspects, these adjuncts 1000, 1000' can be substantially the same in size, shape, and configuration.

Figure 18:
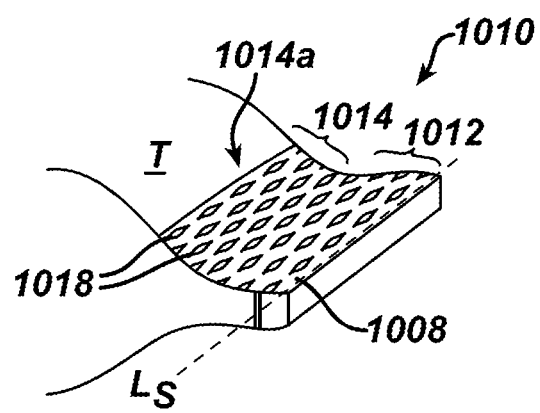
FIG. 18 is a perspective view of another exemplary embodiment of adjunct material stapled to tissue.

Another embodiment of an adjunct 1010 is shown in FIG. 18 and also includes a central region and wing region. In this embodiment, a wing portion 1014 has a plurality of openings 1018 formed therein which can allow the wing portion 1014 to flex with the tissue T during expansion and contraction of the tissue T. The openings 1018 can have various sizes, shapes, and configurations, and can be circular, oval, rectangular, etc., and can be positioned at various locations across the wing portion 1014. In the illustrated embodiment, the openings 1018 are slits positioned in multiple rows, the rows being substantially parallel to the longitudinal axis LC of a central region 1012. A longitudinal axis of the slits 1018 can be parallel to a longitudinal axis LS of the staples 1008. A number of longitudinal rows and a number of openings 1018 disposed in each row can vary. In the illustrated embodiment, a row adjacent to the central region 1012 can have a smaller number of openings 1018 than a row adjacent to an outermost edge 1014*a* of the wing portion 1014. For example, the row adjacent to the central region 1012 can have about three openings 1018 formed therein while the row adjacent to the outermost edge 1014*a* of the wing portion 1014 can have about four openings 1018 formed therein. In this way, a flexibility of the wing portion 1014 can increase from the central region 1012 to the lateral edge and can further facilitate distribution of strain across the tissue T.

Figure 19A:
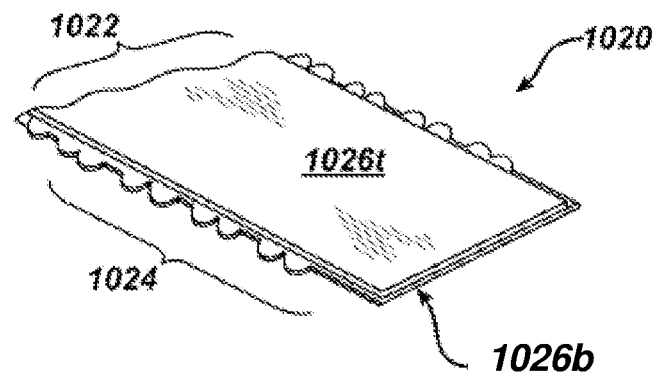
FIG. 19A is a perspective view of an adjunct material having edge protrusions configured to distribute a strain to tissue beyond a staple line.
Figure 19B:
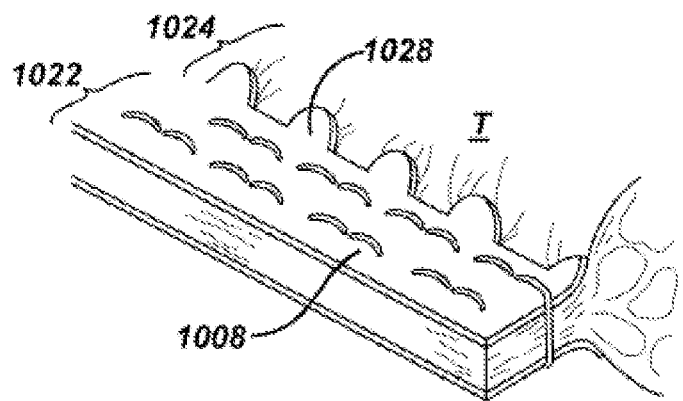
FIG. 19B is a perspective view of another adjunct material having edge protrusions, the adjunct material being stapled to tissue.

FIGS. 19A and 19B illustrate another embodiment of a tissue adjunct having wings for distributing strain across the tissue. FIG. 19A illustrates an adjunct 1020 having a central region 1022 and a wing region 1024, both regions being formed from a plurality of layers. As in the previous embodiments, the central region 1022 can have a substantially rectangular shape. A top layer of material can define the central region 1022 and both regions 1022, 1024 can be formed from a plurality of layers. The central region 1022 can have a substantially rectangular shape, but can be shaped in other ways. As shown in FIG. 19A, a top layer of material 1026*t* can define the central region and can be formed from a flexible material, such as PDS®, PGA, Neoveil®, ORC or other polymers and biologically derived material constructs or combinations disclosed herein. Material geometry and structure (material thickness, fiber orientation, polymer chain orientation, hole patterns, etc.) may be used to create desired isotropic or anisotropic deformation characteristics. A bottom layer of material 1026*b* can also be substantially flexible, and in certain aspects can have a greater flexibility than the top layer 1026*t*. The bottom layer 1026*b* can have a shape that corresponds to a shape of the top layer 1026*t*, and is shown having a substantially rectangular shape. The bottom layer 1026*b* can have a larger surface area than the top layer 1026*t* such that the bottom layer 1026*b* extends beyond lateral edges of the top layer 1026*t*. As shown, lateral edges of the bottom layer 1026*b* can be scalloped, having a plurality of semicircular protrusions 1028 along the wing portion 1024. These semicircular protrusions can be spaced at equal distances apart along the edges, or can be spaced in groups of two, three, four, and the groups of protrusions can be disposed at equal distances apart along the edge. When the adjunct 1020 is stapled to tissue, the top layer 1026*t* of material 1026*t* will be positioned away from and will not directly contact the tissue, while the bottom layer 1026*b* will directly contact tissue. Additionally, the protrusions can be positioned away from the staple rows and can distribute a strain across the tissue T to prevent formation of leaks. The bottom layer 1062*b* may be formed from a flexible material, such as PDS®, PGA, Neoveil®, ORC or other polymers and biologically derived material constructs or combinations disclosed herein. Material geometry and structure (material thickness, fiber orientation, polymer chain orientation, hole patterns, etc.) may be used to create desired isotropic or anisotropic deformation characteristics. In an embodiment, at least one of top layer 1062*t* and bottom layer 1062*b* is at least partially comprised of PDS® to aid in attachment of adjacent layers. In an embodiment, both the top layer 1062*t* and bottom layer 1062*b* are created from absorbable materials.

The adjunct material can be constructed in various ways. For example, the adjunct material can be formed from a continuous material. That is, as shown in FIG. 19B, the adjunct 1020 can include a single layer with the central region 1022 and the wing portion 1024 having the plurality of protrusions 1024 for distributing a strain. In other aspects, the adjunct can include more than two layers of material. For example, one or more intermediate layers of material (not shown) can be positioned between the top layer and the bottom layer and can be more rigid than the top and bottom layers. The layers can be coupled together using known manufacturing techniques, such as lamination, adhesive, etc. The protrusions 1028 on the wing portion 1024 of the adjunct can also be formed using known manufacturing techniques, such as laser cutting, stamping, punching, etc.

Figure 20:
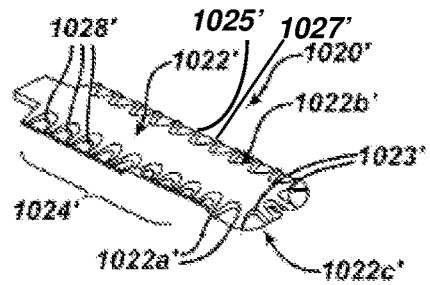
FIG. 20 is a perspective view of an adjunct material including an outer region with a plurality of cuts formed therein.

Another exemplary adjunct is shown in FIG. 20 and includes a wing region having a varied geometry. As shown, an adjunct 1020' can have a wing region 1024' extending around a perimeter of the central region 1022' and can have a plurality of surface features 1028' formed therein and spaced evenly along the wing region 1024'. The surface features 1028' can be generally shaped as a boomerang and can include an elbow 1023' and first and second arms 1025', 1027' extending therefrom. As shown in FIG. 20, the elbow 1023' can be positioned along edges 1022*a'*, 1022*b'*, 1022*c'* of the central region 1022' while terminal ends of the arms 1025', 1027' can be positioned at an outer edge of the wing region 1024'. In this way, a thickness of the wing region 1024' in a direction transverse to a longitudinal axis of the central region 1022' can vary and a thickness of the wing region 1024' in a direction parallel to the longitudinal axis of the central region 1022' can also vary. These surface features 1028' can be formed by removing a portion of the adjunct material 1020' using known manufacturing techniques, such as laser cutting, stamping, punching, etc.

Figure 21A:
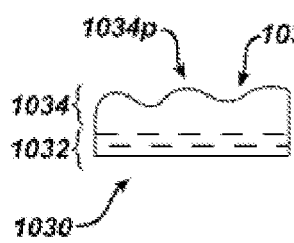
FIGS. 21A-21C are side views of adjunct material having modified outer regions.
Figure 21B:
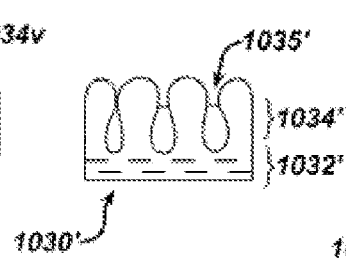
Figure 21C:
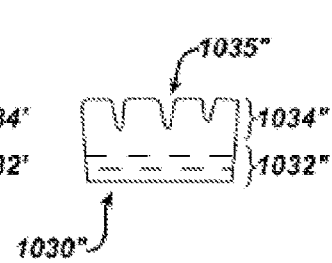
Figure 21D:
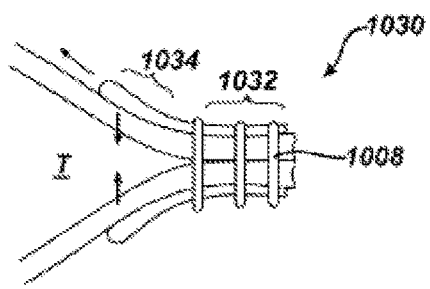
FIG. 21D is a side, cross-sectional view of adjunct material stapled to a body lumen.

FIGS. 21A-21C illustrate adjunct material including wing portions with modified edges. For example, a wing portion 1034 of an adjunct 1030 of FIG. 21A can have an outer edge in the shape of a sine wave with peaks 1034*p* and valleys 1034*v* along its length so that the wing portion 1034 is atraumatic and does not increase a likelihood of forming leaks in tissue. A wing portion 1034' of FIG. 21B includes a first material forming a central region 1032' and the wing portion 1034', the wing portion 1034' having curved edges which loop around and extend toward the central region 1032', and back toward the edge forming an oblong opening 1035'. In certain aspects, a second material is disposed in the oblong, teardrop shaped openings 1035', such as by being laminated to the first material to form the adjunct 1030'. A thickness of this second material can vary from a thickness of the first material. For example, the thickness of the second material can be less than the thickness of the first material 1036', as shown. A wing portion 1034" of FIG. 21C can have a plurality of openings 1035" formed therein, such as triangular shaped openings, that can form protrusions similar to those protrusions 1028 shown in FIG. 19B, but the protrusions can have corners rather than rounded edges. The adjuncts 1030, 1030', 1030" of FIGS. 21A-21C can be formed from different materials, such as any flexible or stretchable polymer material described herein. In use, any one of the adjuncts 1030, 1030', 1030" can be stapled to tissue and any of the respective wing portions can extend beyond the staple line. A shown in FIG. 21D, the adjunct 1030 can be stapled to tissue T and the wing portion 1034 can be positioned outside of the staples 1008 which form a staple line and the central portion 1032 can be positioned inside of the staple line. In certain aspects, as the tissue expands and contracts, the adjuncts can stretch or flex in a direction transverse to the staple rows or can be configured to stretch in multiple directions, such as along an outer surface of the tissue T as shown. A person skilled in the art will appreciate that the edges of the wing portions can be shaped in other ways than the illustrated embodiments.

Figure 22A:
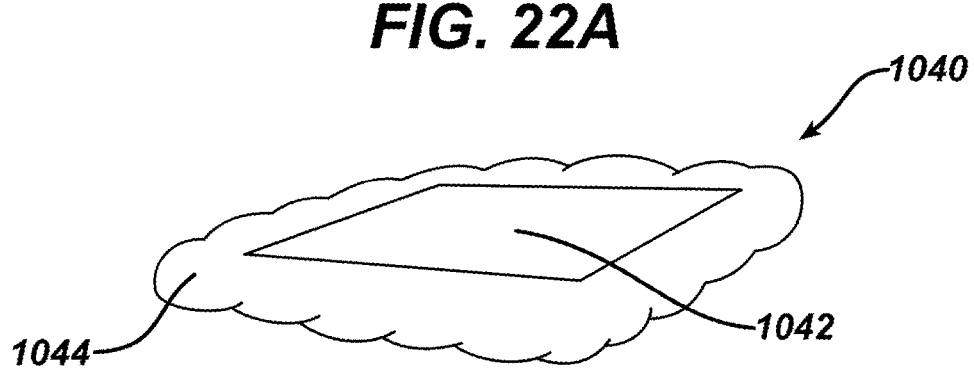
FIG. 22A is a perspective view of adjunct material having first and second layers and woven, atraumatic edges.
Figure 22B:
FIG. 22B is a side view of the adjunct material of FIG. 22A showing the first and second layers.
Figure 22C:
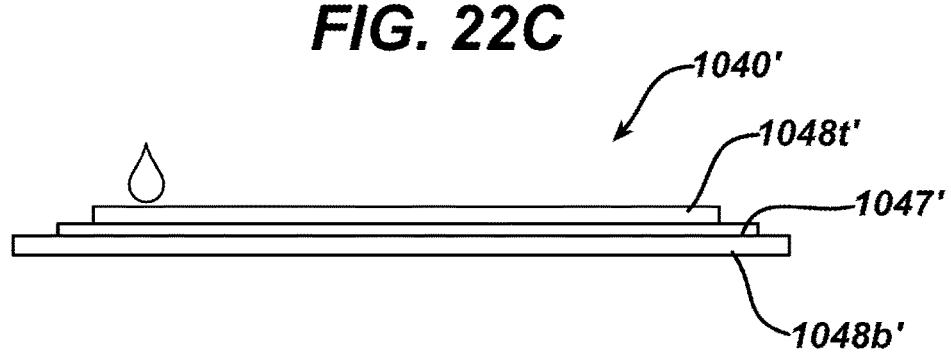
FIG. 22C is a side view of the adjunct material of FIG. 22A absorbing fluid in between the first and second layers.

FIGS. 22A-22C illustrate another embodiment of adjunct material including a wing portion with modified edges. As shown in FIG. 22A, an adjunct material 1040 can be woven. A central region 1042 of the adjunct 1040 can be formed from a woven material of higher density than a woven material at a wing portion 1044 of the adjunct 1040. In other aspects, a less dense woven material can encase a denser woven material on all sides, as shown in FIG. 22B. In both embodiments, the wing portion 1044 can have soft, atraumatic edges 1046 that have a decreased likelihood of puncturing or otherwise damaging the tissue and causing holes to form therein. The adjunct 1040 can be configured to wick and/or absorb liquid therein. For example, in the embodiment of FIG. 22C, a top layer 1048t' of material of an adjunct 1040' is shown positioned over a bottom layer of material 1048b', liquid 1047' being wicked through the top layer of material and into a space between the top and bottom layers 1048b', 1048t'. These adjunct materials can be formed from various woven materials known in the art, such as ETHISORB® (Ethicon, Inc., Somerville, N.J.). In one embodiment, central region 1042 may be a film comprised of solid, but deformable absorbable material.

Figure 23A:
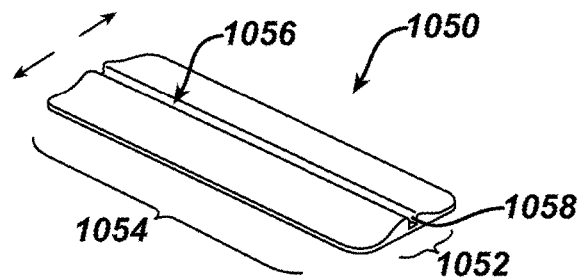
FIG. 23A is a perspective view of adjunct material having a variable thickness in a lateral direction.
Figure 23B:
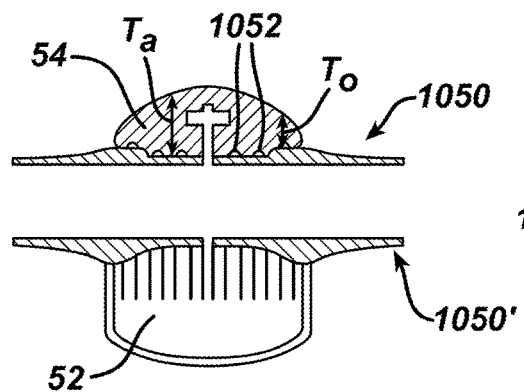
FIG. 23B is an end view of an anvil and cartridge assembly and two variable thickness adjuncts, a first adjunct material associated with the anvil and a second adjunct material associated with the cartridge assembly.
Figure 23C:
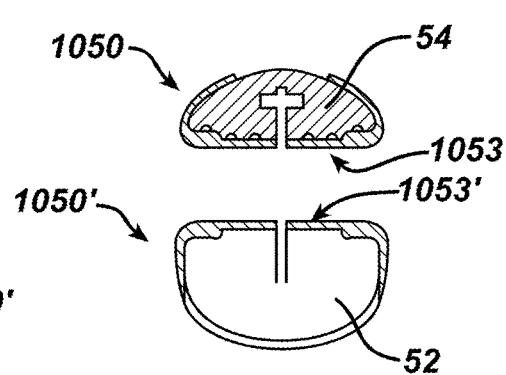
FIG. 23C is an end view of the anvil and cartridge assembly of FIG. 23B having the first and second adjunct materials coupled thereto.
Figure 23D:
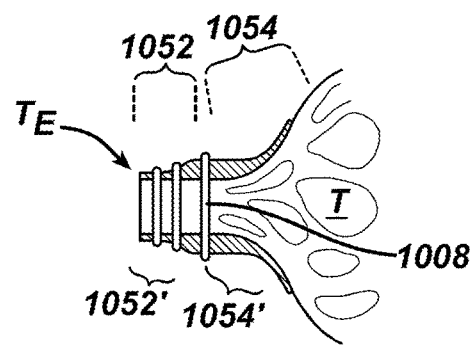
FIG. 23D is a side view of the first and second adjunct material stapled to tissue.

An adjunct material for use with a stapler that deploys variable thickness staples is shown in FIGS. 23A-23D. As shown, a thickness of an adjunct 1050 can vary from a central axis 1056 to an outer edge of the adjunct 1050 in a lateral direction indicated by arrows. That is, the adjunct 1050 can have a decreasing/tapering thickness from the central axis 1056 of the adjunct 1050 to the outer edge thereof in the lateral direction. As in the previous embodiments, the adjunct material 1050 can include a central region 1052 and wing portion 1054. The adjunct 1050 can include an elongate slot 1058 formed along the central axis 1056 of the adjunct 1050 and having a size and shape that corresponds to a size and shape of a cutting member (not shown). In the illustrated embodiment, the elongate slot 1058 has a substantially rectangular shape. FIGS. 23B and 23C provide end views of a cartridge assembly 52 and an anvil 54 having a varying thickness in a lateral direction such that the stapler 10 can deploy staples (not shown) of varying heights. As shown, a thickness $T_a$ of the anvil 54 near the cutting member slot can be greater than a thickness $T_o$ of the anvil 54 near its lateral edge. The adjunct 1050 can be coupled to the cartridge assembly 52 and/or to the anvil 54 with at least the central region 1052 of the adjunct 1050 directly contacting the tissue-contacting surface 60, 58 of the cartridge assembly 52/anvil 54. The tissue-contacting surface 58 of the anvil 54 can include one or more mating points attaching the adjunct 1050 to the anvil 54, as shown. The wing portion 1054 of the adjunct 1050 can be folded around the cartridge assembly 52 and/or the anvil 54 and attached thereto, as will be described in greater detail below. In this way, a tissue-contacting surface 1053 of the first adjunct 1050 can be substantially planar and can be disposed parallel to a tissue contacting surface 1053' of the second adjunct 1050' disposed on the cartridge assembly 52. When the adjuncts 1050, 1050' are stapled onto tissue, as shown in FIG. 23D, the wing portion of the adjunct 1050 can be disposed between the staples 1008 and extend toward a cut terminal end $T_E$ of the tissue T, while a second portion of the adjunct 1050 can extend away from the cut terminal end $T_E$ of the tissue T and distribute strain to the tissue T, similar to the wing portions described above. The adjunct 1050' can have similarly positioned portions 1052', 1054', as shown.

Figure 24A:
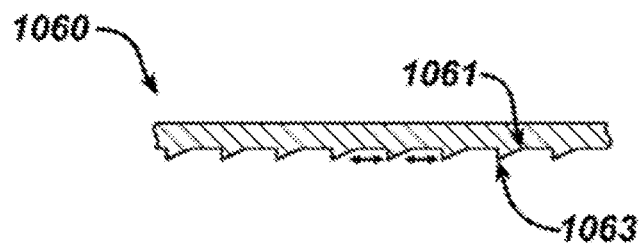
FIG. 24A is a side view of an adjunct material having surface features formed thereon for penetrating and gripping into tissue.
Figure 24B:
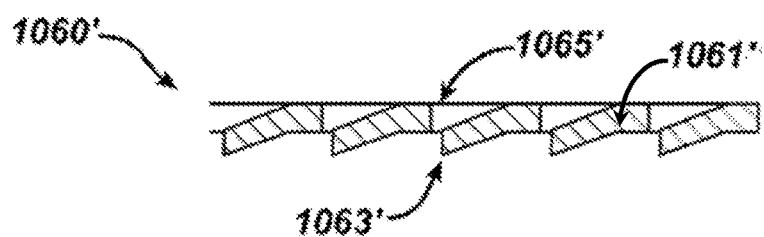
FIG. 24B is a side view of another adjunct material having surface features for penetrating and gripping into tissue.
Figure 24C:
FIG. 24C is an end view of four rows of adjunct material, each row of adjunct material having a surface feature locked in a tissue.
Figure 24D:
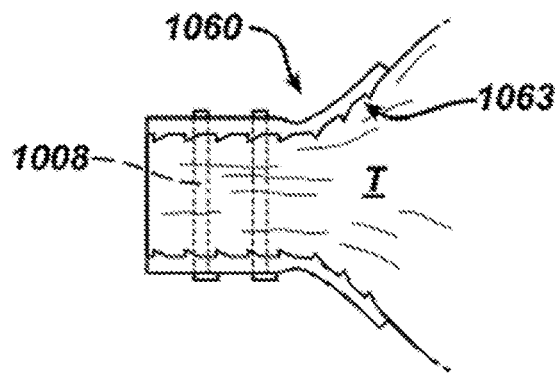
FIG. 24D is a side view of an adjunct material having surface features penetrated into tissue.
Figure 25A:
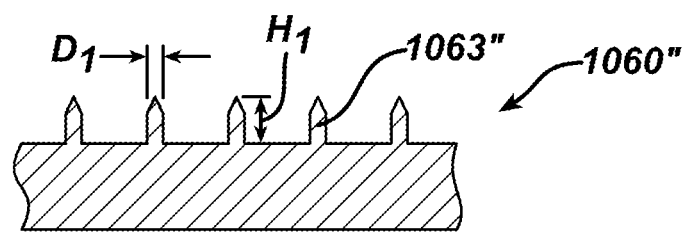
FIG. 25A is a side view of another exemplary adjunct material having a plurality of pointed surface features for penetrating into tissue.
Figure 25B:
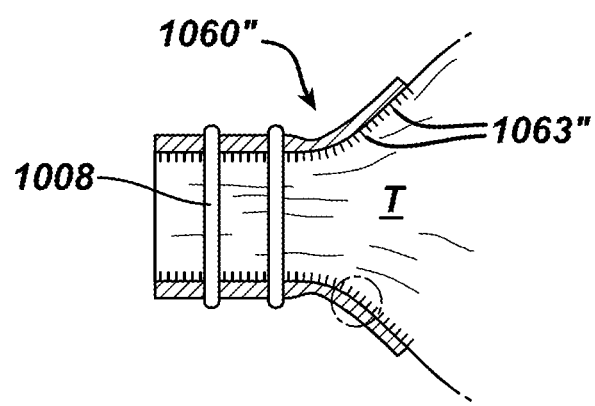
FIG. 25B is a side view of the adjunct material of FIG. 24A having the pointed surface features piercing into tissue.

Any of the adjunct materials can include various features for increasing friction between the adjunct material and the tissue to ensure that the adjunct material remains in a desired position. For example, adjuncts 1060, 1060' in FIGS. 24A and 24B include a plurality of teeth 1061, 1061' formed on a tissue-contacting surface thereof and terminating in points 1063, 1063' that can penetrate into tissue. As shown, the plurality of teeth 1061, 1061' can be spaced at equal distances apart in the lateral direction of the adjunct 1060, 1060'. The teeth 1061, 1061' can be formed in the adjunct 1060, 1060' using various known manufacturing techniques, such as via compression molding, cut/stamping, punching, etc. For example, the adjunct 1060 of FIG. 24A can be compression molded while the adjunct 1060' of FIG. 24B can be formed from stamping slits 1065' into material to form the teeth 1061'. The gaps between the teeth 1061, 1061' can push into tissue T and create a lock that prevents sliding of the adjunct 1060, 1060', as in FIG. 24C which illustrates multiple rows of adjuncts 1060'. In another embodiment shown in FIG. 25A, the adjunct 1060" can include a plurality of micropillars 1063" formed on a tissue-contacting surface thereof, the micropillars 1063" being shaped as needles configured to penetrate into tissue T. The teeth 1061, 1061' and/or micropillars 1063" can directly penetrate into the tissue T as shown in FIGS. 24D and 25B and can thereby prevent the adjunct 1060, 1060" from sliding relative to the staples 1008 as the tissue T expands and contracts. In certain aspects, the micropillars 1063" can have a diameter D1 in the range of about 0.01 to 0.50 mm and a height H1 in the range of about 0.05 to 0.50 mm.

Figure 26A:
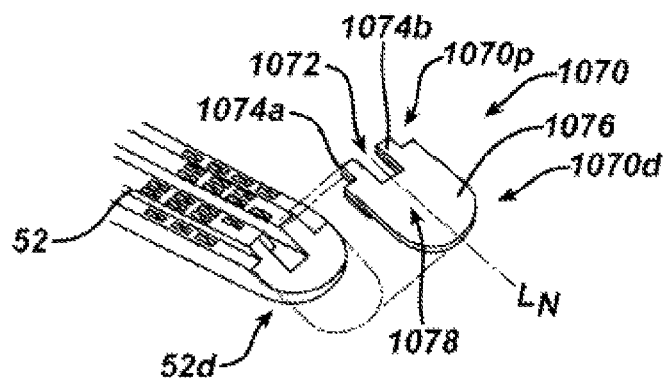
FIG. 26A is a perspective view of a cartridge assembly having an adjunct material for detachable coupling to a distal end of the cartridge assembly.
Figure 26B:
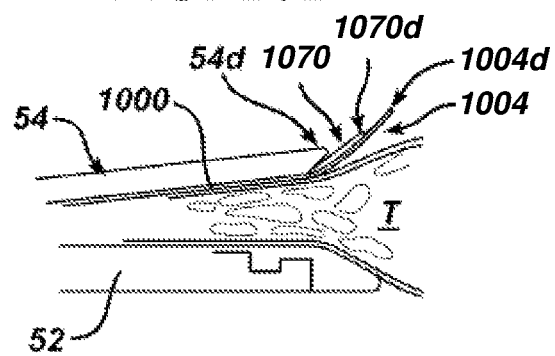
FIG. 26B is a side view of the cartridge assembly and an anvil of a surgical stapler grasping tissue with the adjunct material of FIG. 26A extending beyond a distal end of the cartridge assembly.
Figure 26C:
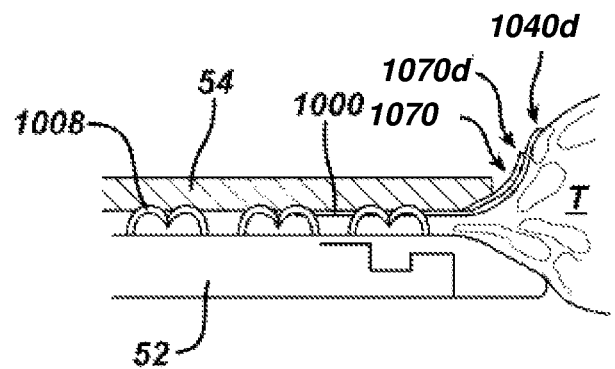
FIG. 26C is a side view of the cartridge assembly and the anvil of FIG. 26B deploying staples through the adjunct material and the tissue.

Another embodiment of an adjunct material is shown in FIGS. 26A-26C. In this embodiment, an adjunct material such as the adjunct 1000 of FIGS. 17A and 17B is used in conjunction with a nose extension member 1070 that can be coupled to an anvil 54 and/or a cartridge assembly 52 of a surgical stapler 10. As shown in FIG. 26A, a distal end 1004d of the adjunct 1000, that is, the distal end 1004d of the wing portion 1004 can terminate at or proximal to a distal-most end 52d of the cartridge assembly 52. As shown in FIG. 26B, a distal end 1004d of the adjunct 1000, that is, the distal end 1004d of the wing portion 1004 can terminate at or proximal to a distal-most end 54d of the anvil 54. The nose extension member 1070 can be added onto the cartridge assembly 52 and/or the anvil 54 to replace or supplement a distal portion of the adjunct material 1000. A proximal end 1070p of the nose extension member 1070 can have a cutout 1072 formed therein and sized so as to not obstruct or cover a slot formed in the anvil 54 for receiving a cutting member (not shown). The cutout 1072 can define first and second extension arms 1074a, 1074b which can be releasably coupled to the distal end 54d of the anvil 54 along a curved portion of the anvil 54 that is distal to the anvil's 54 tissue contacting surface in various ways, such as using an adhesive. A distal-most end 1070d of the nose extension member 1070 can be substantially rounded. A mechanism for releasing a distal portion 1076 of the nose extension 1070 from the proximal end 1070p of the nose extension 1070 can also be provided. In certain aspects, this releasing mechanism can consist of a perforation 1078 extending transverse to a longitudinal axis LN of the nose extension member 1070. In use, an adjunct 1000 can be positioned on the anvil 54 and the nose extension member 1070 can also be coupled to the anvil 54. The anvil 54 and cartridge assembly 52 can grasp tissue T therebetween, and a portion of the adjunct 1000 can extend distally beyond the nose extension member 1070, as shown in FIG. 26B. That is, the distal end 1070d of the nose extension member 1070 can be positioned distal to the distal end 1004d of the adjunct 1000. The anvil 54 and the cartridge assembly 52 can deploy staples 1008 through the tissue T and through the adjunct 1000, while the wing region 1004 of the adjunct 1000 does not include staples 1008 extending therethrough. The wing region 1004 of the adjunct 1000 can directly contact the tissue T and the nose extension member 1070 can be positioned above the wing region 1004. In certain aspects, the nose extension member 1070 can be a semi-flexible material and can be used in conjunction with the adjunct 1000 to help relieve a strain on tissue T and/or provide strength to the adjunct 1000. In use, the distal end of the nose extension member 1070 can be removed from the anvil 54 and/or the cartridge prior to, during, and/or after the tissue T is stapled.

While features of the adjunct described above were illustrated as separate embodiments, an adjunct can have any combination of features described above.

Mechanisms for Attaching and Releasing Adjuncts from an End Effector

Figure 27A:
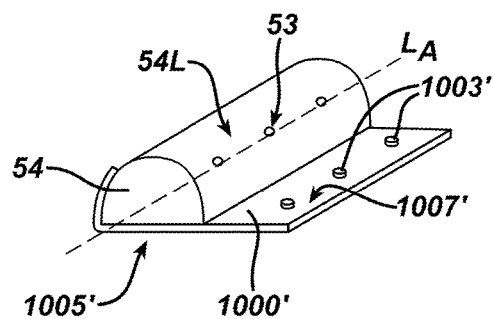
FIG. 27A is a perspective view of adjunct material having protrusions configured to mate with corresponding depressions formed in a cartridge assembly.
Figure 27B:
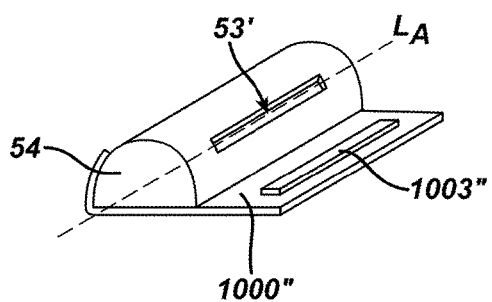
FIG. 27B is a perspective view of adjunct material having a single protrusion configured to mate with a corresponding depression formed in a cartridge assembly.

Various mechanisms can be used to attach and then release an adjunct having wings from an end effector, e.g. a cartridge assembly 52 or an anvil 54. While the embodiments described below include features formed on an anvil 54, any of these features can be formed on a cartridge assembly 52 for mating an adjunct to the cartridge assembly 52. FIGS. 27A-27B illustrate adjunct material 1000', 1000" having mating features keyed to corresponding mating features formed on an anvil 54. More specifically, FIG. 27A shows an adjunct 1000' having a plurality of cylindrical protrusions 1003' formed on a surface 1007' that is oriented away from a tissue contacting surface 1005' of the adjunct 1000'. While FIG. 27A illustrates three cylindrical protrusions 1003' spaced apart along an axis parallel to a longitudinal axis LA of the anvil 54, any number of protrusions 1003' can be formed at various locations along the adjunct 1000'. A lateral surface 54L of the anvil 54 can have a plurality of depressions 53 configured to receive the plurality of protrusions 1003' from the adjunct 1000' therein. In one embodiment, a height (not shown) of the cylindrical protrusions 1003' can vary, and can be in the range of about 0.25 to 1.00 mm, the height measured perpendicular to the surface 1007' of the adjunct 1000'. The protrusions 1003' formed on the adjunct 1000' can have other sizes and shapes. As shown in FIG. 27B, in another embodiment, an adjunct 1000" can have a single elongate rectangular protrusion 1003" extending parallel to the longitudinal axis LA of the anvil 54. A lateral surface of the anvil 54 can also include a corresponding elongate rectangular depression 53' for receiving the rectangular protrusion 1003" therein when the adjunct 1000" is folded around the anvil 54. A height (not shown) of the rectangular protrusion 1003" can also vary, but can be in substantially the same range as the height of the cylindrical protrusions 1003' described above. While only a first lateral surface 54L of the anvil 54 is shown in FIGS. 27A and 27B, a person skilled in the art will appreciate that identical protrusion(s) can be formed on a second lateral surface (not shown) of the anvil 54. Similarly, identical depression(s) can be formed on a second lateral surface (not shown) of the adjuncts 1000', 1000".

Figure 28A:
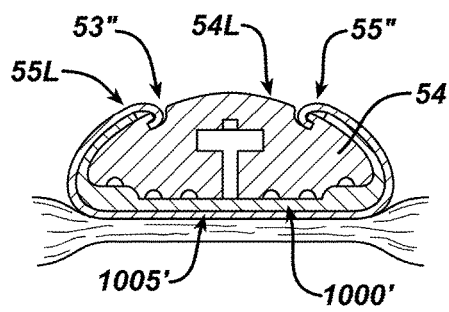
FIG. 28A is an end view of an adjunct material extending around a cartridge assembly and having first and second lateral edges coupled to the cartridge assembly.
Figure 28B:
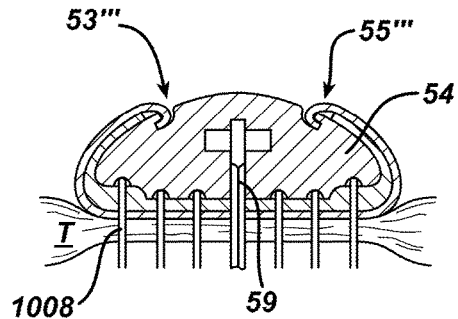
FIG. 28B is an end view of the adjunct material and the cartridge assembly of FIG. 27A and a cutting member being advanced through the cartridge assembly to release the adjunct material from the cartridge assembly.
Figure 29A:
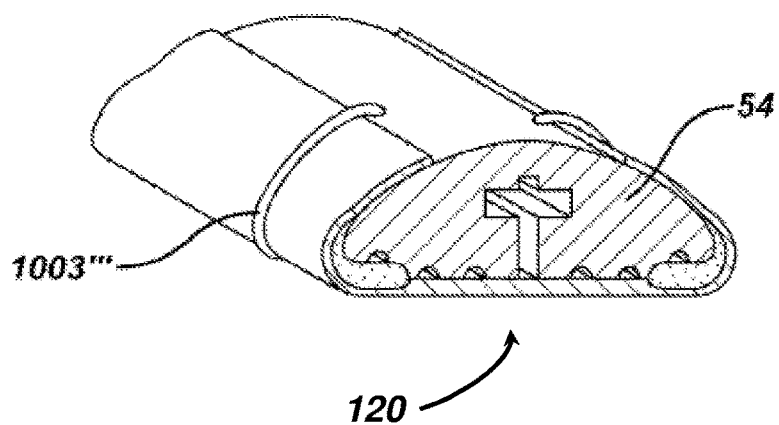
FIG. 29A is a perspective view of a cartridge assembly including suture coupling an adjunct material to the cartridge assembly.
Figure 29B:
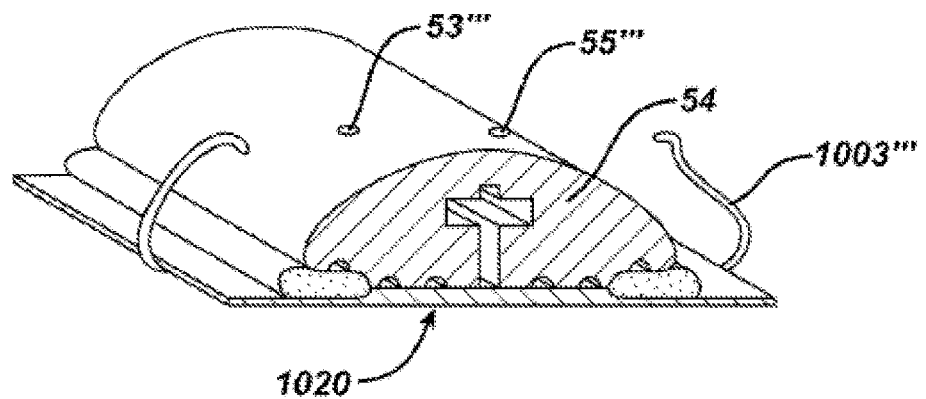
FIG. 29B is a perspective view of the cartridge assembly and adjunct material of FIG. 29A, the suture detached from the cartridge assembly to release the adjunct material.

An adjunct can be coupled to an anvil/cartridge assembly in other ways. As shown in FIGS. 28A and 28B, a strand of suture can couple the adjunct to the anvil 54. The suture can extend from the first lateral surface 54L of the anvil 54, across the tissue-contacting surface of the adjunct, and to the second lateral surface 55L of the anvil 54. First and second depressions 53''', 55''' can be formed in the first and second lateral surfaces of the anvil 54, and a first terminal end of the suture can be received in the first depression 53''' and a second terminal end can be received in the second depression 55'''. A length of the suture and/or a size of the depressions 53''', 55''' can be selected so that the suture is taut when the terminal ends of the suture 1003''' are positioned within the depressions 53''', 55'''. As a cutting member 59 advances through the anvil 54 during and/or after the staples 1008 are deployed into the tissue T, as shown in FIG. 28B, the cutting member 59 can sever the suture, causing the terminal ends of the suture 1003''' to slide out of the depressions 53''', 55''' and thereby releasing the adjunct from the anvil. FIGS. 29A and 29B illustrate the strand of suture 1003''' extending around an anvil 54 and coupling a multilayer adjunct 1020 to the anvil 54. As in the previous embodiment, advancement of the cutting member (not shown) relative to the anvil 54 can sever the suture 1003''' and release the suture 1003''' from the depressions 53''', 55''' in the anvil 54 to release the adjunct 1020. As will be appreciated by a person skilled in the art, any number of strands of suture can be used to couple the adjunct to one of the cartridge assembly 52 and the anvil 54 and the depressions formed therein can vary so long as they are configured to receive a portion of the suture therein.

Figure 30A:
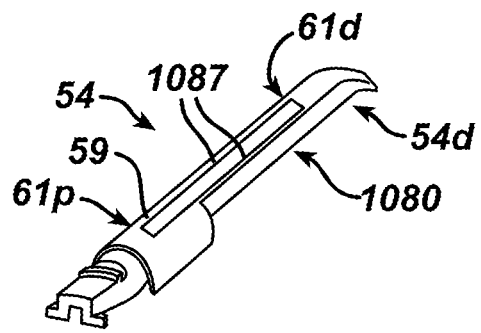
FIG. 30A is a perspective view of a shaft of a surgical stapler including an adjunct material coupled thereto.
Figure 30B:
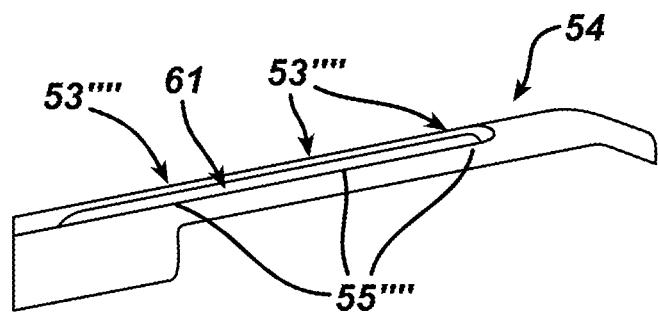
FIG. 30B is a side view of the shaft of FIG. 30A showing attachment points for attaching the adjunct material to the shaft.
Figure 30C:
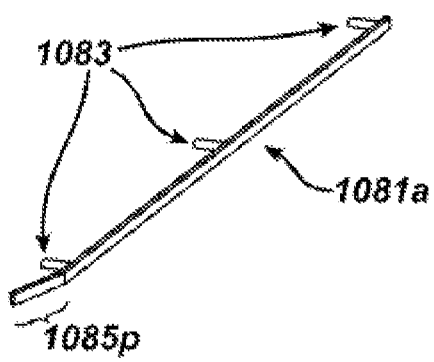
FIG. 30C is a perspective view of a driver insertable within the shaft and having a plurality of lateral extension portions.
Figure 30D:
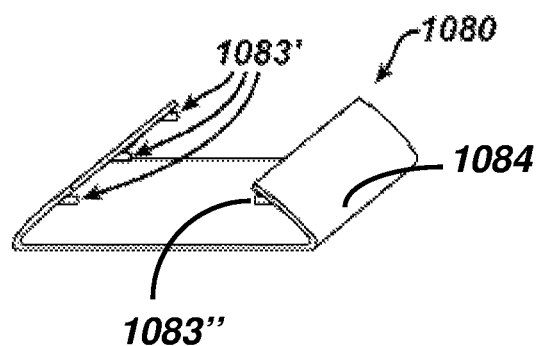
FIG. 30D is a perspective view of adjunct material for attaching to the shaft.
Figure 30E:
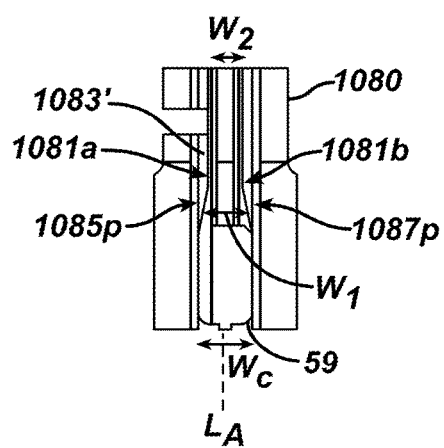
FIG. 30E is a partial top view of the shaft of FIG. 30A with a cutting member of the stapler in a first, retracted position.
Figure 30F:
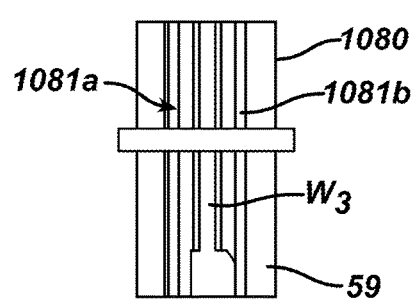
FIG. 30F is a partial top view of the shaft of FIG. 30A with the cutting member in a second, advanced position that releases the adjunct material from the shaft.

FIGS. 30A-30B illustrate other mechanisms for attaching an adjunct to an anvil/cartridge assembly. In this embodiment, the anvil 54 of a surgical stapler 10 includes a cutting member 59 that can advance within a slot 61, referred to as a longitudinal track, and can move between proximal and distal ends 61p, 61d of the track 61. A driver including first and second elongate members (not shown) can be disposed in the longitudinal track 61, as in FIG. 30B. Three cylindrical protrusions (not shown) extend from the elongate members and into depressions 53"", 55"" formed in both lateral surfaces of the anvil 54, but there can be any number of protrusions spaced along the driver and having various other shapes. As shown in FIG. 30C, a first driver 1081a can be generally elongate and can have a plurality of protrusions 1083, such as three protrusions 1083, oriented transverse to a longitudinal axis of the driver, the protrusions 1083 being cylindrical shaped. A wing portion 1084 of an adjunct material 1080 can be disposed around a lateral surface of the anvil 54 and can include a plurality of protrusions 1083' oriented transverse to the longitudinal axis LA of the anvil 54 when the adjunct material 1080 is coupled thereto. As shown in FIG. 30D, the adjunct material 1080 can have a first set of protrusions 1083' for mating with the first lateral surface of the anvil 54 and a second set of protrusions 1083" for mating with the second lateral surface of the anvil 54. Prior to use, the first driver 1081a can be positioned on a first lateral wall of the track 61 and the second driver 1081b can be positioned on a second lateral wall of the track 61. A proximal end of each driver 1081a, 1081b can have an angled portion 1085p, 1087p such that when the drivers 1081a, 1081b are disposed in the track 61, a width W1 between the drivers 1081a, 1081b at a proximal end of the track 61 is greater than a width W2 between the drivers 1081a, 1081b at and/or distal to the protrusions 1083', the width being measured transverse to the longitudinal axis LA of the anvil 54 as shown in FIG. 30E. Additionally, the width W2 between the drivers 1081a, 1081b distal to the proximal end 61p of the track 61 can be less than a width WC of the cutting member 59. In this way, the cutting member 59 can be advanced toward the distal end 54d of the anvil 54 and can increase a width between the drivers 1081a, 1081b and the protrusions 1083 can push the corresponding protrusions 1083' on the adjunct 1080 off of and away from the anvil as in FIG. 30F, thereby releasing the adjunct from the anvil 54. In certain aspects, the adjunct 1080 can be biased to a flattened, substantially planar configuration such that when the cutting member 59 advances within the track 61 and exerts a force on the drivers 1081a, 1081b, the adjunct 1080 is more able to release from the anvil 54.

Figure 31A:
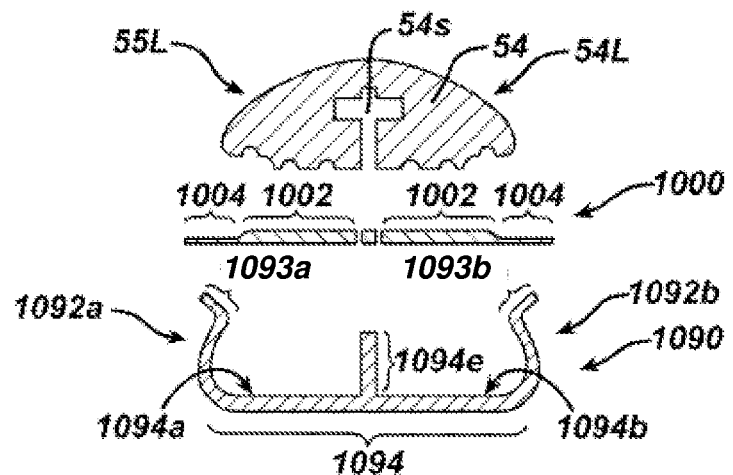
FIG. 31A is an end view of a cartridge assembly, an adjunct material, and an insertion tool for attaching the adjunct material to the cartridge assembly.
Figure 31B:
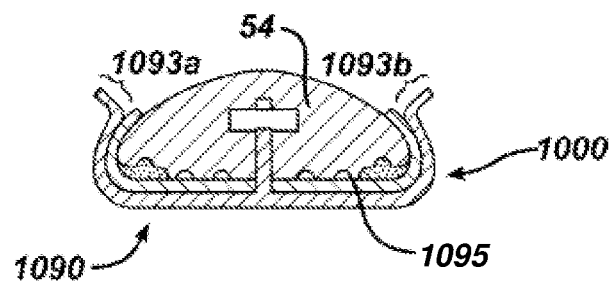
FIG. 31B is an end view of the insertion tool pressing the adjunct material onto the cartridge assembly of FIG. 31A.
Figure 31C:
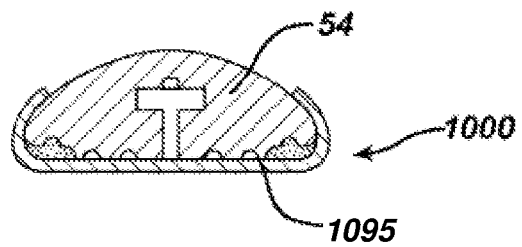
FIG. 31C is an end view of the cartridge assembly of FIG. 31A having the adjunct material attached thereto and after the insertion tool has been removed from the cartridge assembly.

A loading mechanism for loading an adjunct onto an anvil/cartridge assembly is shown in FIGS. 31A-3B. A loading mechanism 1090 can have various sizes, shapes, and configurations, and can include a first curved arm 1092a and a second curved arm 1092b having a radius of curvature that corresponds to a radius of curvature of the first and second lateral surfaces 54L, 55L of the anvil 54 and the arms 1092a, 1092b can terminate in angled features 1093a, 1093b that can be grasped by a user. The loading mechanism 1090 can have a planar base 1094 from which each of the first and second curved arms 1092a, 1092b extend. The base 1094 of the loading mechanism 1090 can further include a track extension 1094e extending perpendicular to the base 1094 and disposed along a central longitudinal axis of the loading mechanism 1090 for insertion into the cutting member slot 54s in the anvil 54, as shown in FIG. 31B. A first inner surface 1094a of the loading mechanism 1090 can be defined by the first curved arm 1092a and a first portion of the base 1094 from the first arm 1092a to the track extension, as shown in FIG. 31A. Likewise, a second inner surface 1094b of the loading mechanism 1090 can be defined by the second curved arm 1092b and a second portion of the base 1094 from the second arm 1092b to the track extension 1094e. In this way, the loading mechanism 1090 can be generally E-shaped for receiving the anvil 54. An adjunct 1000 having a central region 1002 and a wing region 1004 can be positioned and sandwiched between inner surfaces of the loading mechanism 1090 and the tissue-contacting surface of the anvil 54, as in FIG. 31B, the loading mechanism 1090 clamping onto the anvil 54 as shown. The track extension 1094e can facilitate achieving a tight fit between the loading mechanism 1090, the adjunct 1000, and the anvil 54 with substantially no gaps between. After the adjunct 1000 is coupled to the anvil 54, such as using any attachment mechanisms described herein, such as attachment mechanisms 1095, the loading mechanism 1090 can be removed from the anvil 54. This can be accomplished, for example, by pressing the angled features 1093a, 1093b of the curved arms away 1092a, 1092b from one another, leaving the anvil 54 loaded with the adjunct 1000 as in FIG. 31C.

Figure 32A:
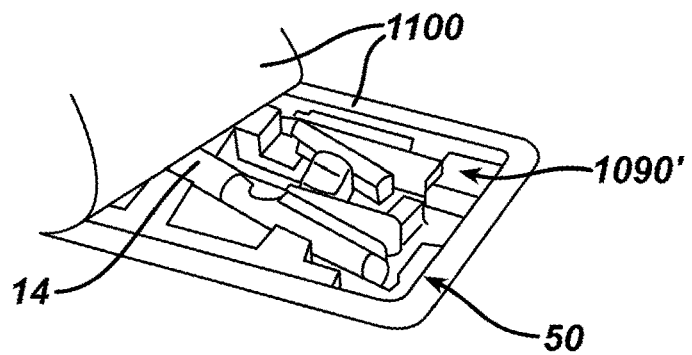
FIG. 32A is an exemplary kit including a retaining tool and a surgical stapler, the retaining tool being configured for wrapping the adjunct material around a cartridge assembly/anvil.
Figure 32B:
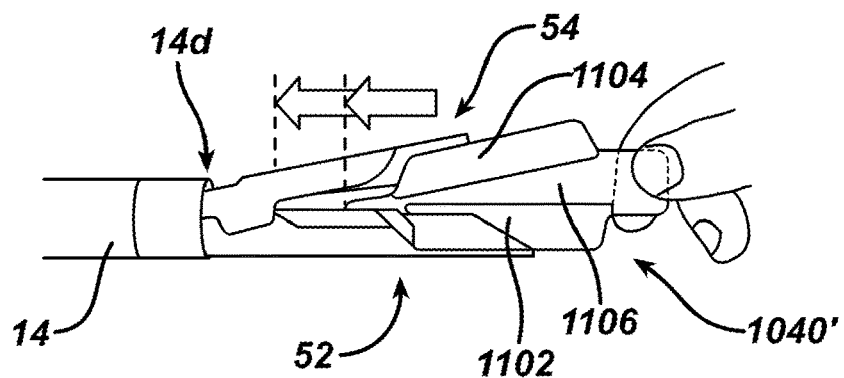
FIG. 32B is a side view of the retaining tool of FIG. 32A being advanced proximally along a longitudinal axis of the anvil and the cartridge assembly.
Figure 32C:
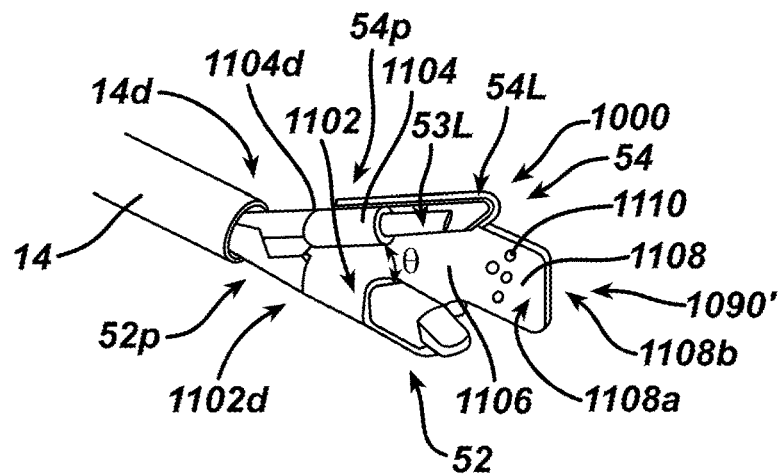
FIG. 32C is a perspective view of the retaining tool and stapler of FIG. 32A, the retaining tool being in a proximal most position.

Another exemplary loading mechanism is shown in FIGS. 32A-32C. A loading mechanism 1090' can be packaged as a kit along with an end effector of a stapler. Alternatively, loading mechanism 1090' may be packaged separately. As in FIG. 32A, the anvil 54 and cartridge assembly 52 of the end effector 50 can include an adjunct material 1000 preloaded thereon or in another non-illustrated embodiment, the adjunct material 1000 can be fixed to the anvil 54 and the cartridge assembly 52 after being removed from packaging 1100. This loading mechanism 1090' can be configured to wrap the wing portion 1004 of the adjunct 1000 around the lateral surfaces 54L, 53L of the anvil/cartridge assembly 54, 52 such that the wing portion is passively coupled to the anvil/cartridge assembly 54, 52. As shown in FIG. 32B, the loading mechanism 1090' can be configured to contact the central region (not shown) of the adjunct 1000 against the tissue-contacting surface of the anvil/cartridge assembly 54, 52 and, if needed, can be configured to shape the wing portion (not shown) around the anvil 54. The loading mechanism 1090' can be formed of a single molded material having an upper retaining portion 1104 and a lower retaining portion 1102, the retaining portions having a channel (not shown) sized and shaped for receiving the anvil/cartridge assembly 54, 52 therein. A shape of the channel can be substantially similar to the shape of the loading mechanism 1090 previously described and can include any of the same features, such as the track extension. The upper and lower retaining portions 1104, 1102 can be disposed at an angle θL relative to one another, the angle being in the range of about 10 to 40 degrees. A support member 1106 can extend between a lower surface of the upper retaining portion 1104 and an upper surface of the lower retaining portion 1102 such that the angle θL between the retaining portions 1102, 1104 is fixed. The support member 1106 can be a substantially solid member, as shown, so as to provide rigidity to the loading mechanism 1090'. A first end of the support member 1106 can terminate in a grasping feature 1108, and the grasping feature 1108 can have first and second planar surfaces 1108a, 1108b configured to be grasped by a user, such as between a thumb and finger of a user. The grasping feature 1108 can further include one or more surface features 1110 for increasing friction between a user's fingers. A longitudinal axis of the grasping feature 1108 can be oriented perpendicular to a longitudinal axis of the stapler 10 or can be parallel to the longitudinal axis of the stapler 10. In use, a user can grasp the grasping feature 1108 and position distal ends 1102d, 1104d of the retaining portions adjacent to proximal ends ends 52p, 54p of the cartridge assembly 52 and the anvil 54. A user can advance the distal end of the loading mechanism 1090' toward the proximal end of the end effector 50, as shown in FIG. 32B, and the retaining portions 1102, 1104 can slide along the anvil/cartridge assembly 54, 52 and force the adjunct material 1000 around the lateral surfaces thereof, as shown in FIG. 32C. This can temporarily secure the wing region 1004 along the lateral surfaces of the cartridge assembly 52 and the anvil 54. With the wing region 1004 so positioned, a user can retract the loading mechanism 1090' in the opposite direction, distally away from the end effector 50, leaving the end effector 50 prepared for insertion into a patient. While reference is made to a single adjunct material 1000 loaded onto the anvil 54, adjunct material 1000' can similar be loaded onto the cartridge assembly 52. The adjunct material 1000, such as the material shown in FIGS. 32A-32C, can be a shape memory material such that the adjunct 1000 is biased to a substantially straightened configuration. That is, when the end effector 50 is positioned inside of the patient, the wing regions can automatically move back to the substantially straightened configuration prior to being deployed off of the end effector 50 and onto tissue.

Delivering Adjuncts into a Patient

Figure 33A:
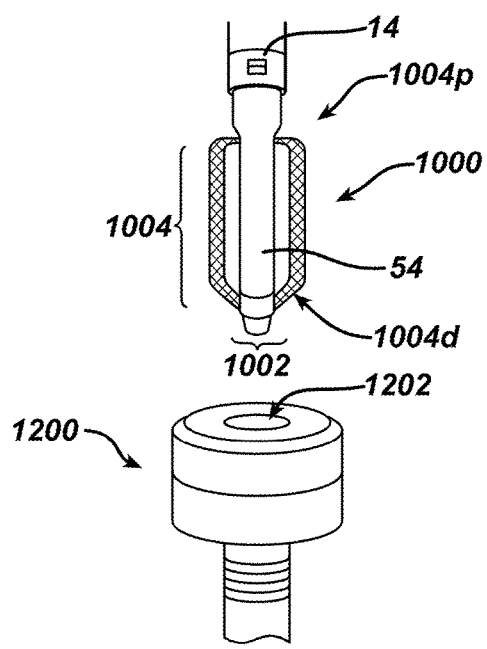
FIG. 33A is a perspective view of an end effector of a stapler having an adjunct material coupled thereto and positioned above a trocar.
Figure 33B:
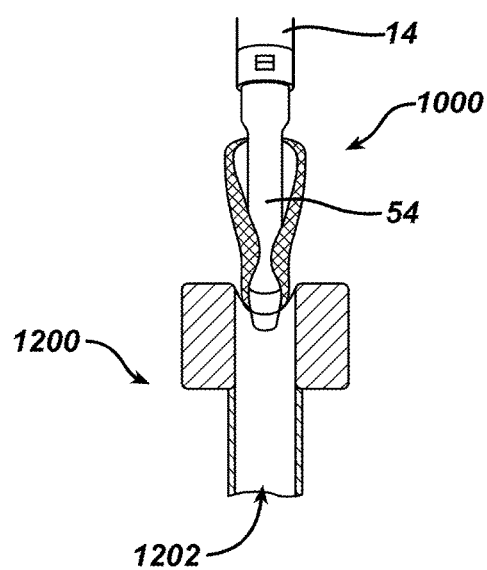
FIG. 33B is a perspective view of the end effector of FIG. 33A having the adjunct material wrapped around the end effector as the end effector is inserted through the trocar.

End effectors having one or more adjuncts coupled thereto can be delivered into various areas of a patient, such as a chest cavity, stomach, etc. As will be appreciated by a person skilled in the art, an adjunct can be delivered through an access port, such as a trocar extending into the patient. Any of the adjuncts herein can include features that assist with delivery of the adjunct into a patient's body. For example, FIG. 33A illustrate an adjunct 1000 having a solid central region 1002 and mesh wing region 1004 coupled to an anvil 54 of a surgical stapler 10. While a single adjunct 1000 is shown coupled to the anvil 54, another adjunct 1000' can be coupled to the cartridge assembly 52 prior to inserting the end effector 50 into a patient's body. A distal portion of the adjunct 1000, such as a distal portion 1004d of the wing region 1004, can be configured to guide proximal portions 1004p of the wing region 1004 around the lateral surfaces (not shown) of the anvil 54 so as to minimize width of the adjunct material, as shown in FIG. 33B. This can facilitate insertion of the end effector 50 and the adjunct 1000 into an access port, such as a port 1202 formed in a trocar 1200, because a width of the anvil/cartridge assembly 54, 52 including the adjunct 1000 thereon will be about the same as a width of the anvil/cartridge assembly 54, 52 without an adjunct. In certain aspects, this distal portion 1004d of the wing region 1004 can be formed from a more rigid material than remaining portions of the wing region 1004 to help guide the adjunct material 1000 into the port 1202.

Stapling Adjuncts onto Tissue

Figure 34A:
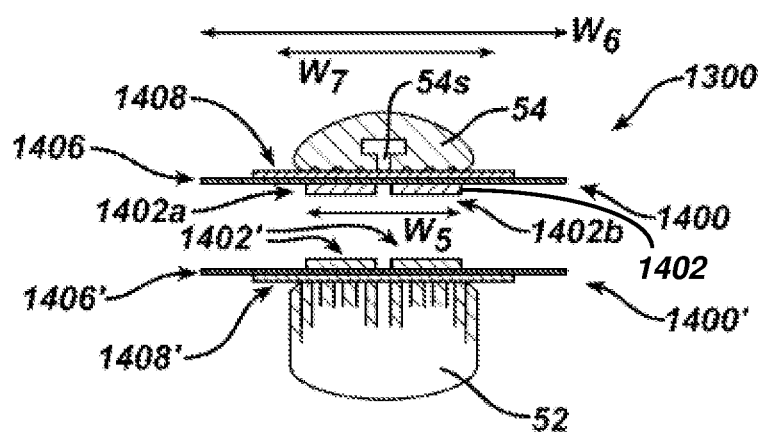
FIG. 34A is an end view of a cartridge assembly and an anvil of a surgical stapler having a multi-layer adjunct material coupled thereto.
Figure 34B:
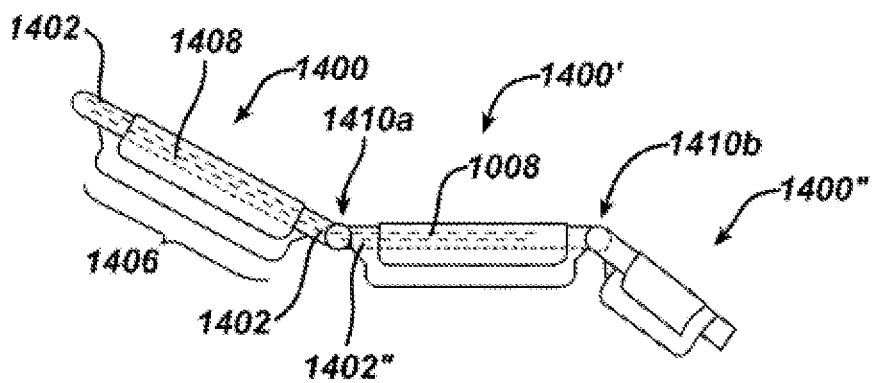
FIG. 34B is a side view of three adjuncts stapled onto tissue and having overlapping portions therebetween.
Figure 34C:
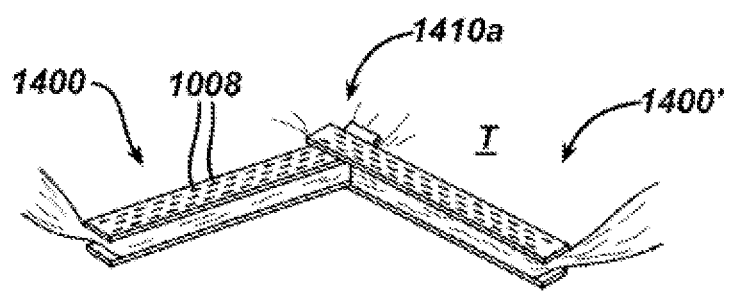
FIG. 34C is a perspective view of a first adjunct material and a second adjunct material stapled onto tissue and having first and second overlapping portions.

An adjunct material can include features facilitating multiple firings of staples along tissue. FIG. 34A illustrates an embodiment 1300 of an end effector 50 having first and second adjunct materials 1400, 1400', the first adjunct material 1400 being coupled to the anvil 54 and the second adjunct material 1400' being coupled to the cartridge assembly 52. As shown, each of the adjunct materials 1400, 1400' can include multiple layers, and the layers can have various widths in the direction transverse to a longitudinal axis (not shown) of the anvil/cartridge assembly 54, 52. A first tissue-contacting layer 1402, 1402' of each adjunct 1400, 1400' can be positioned adjacent to tissue (not shown) when tissue is grasped between the anvil 54 and the cartridge assembly 52. In certain aspects, the first tissue-contacting layer 1402, 1402' can be formed from a material configured to seal around a staple line, such as an elastomeric material. The first tissue-contacting layer 1402, 1402' can have a width W5 in a direction transverse to the longitudinal axis LA of the anvil 54 that is substantially equal to a width WA of the anvil 54, or the width W5 of the first layer 1402 can be less than the width WA of the anvil 54. As shown in FIG. 34A, the first tissue-contacting layer 1402 can include a first portion 1402a positioned on a first side of the cutting member slot 54s and a second portion 1402b positioned on a second side of the cutting member slot 54s rather than being formed from a continuous piece of material. In other aspects, the first layer 1402 can be a single continuous piece of material. A second layer 1406, 1406' can be positioned closer to the tissue-contacting surface of the anvil 54 and can be formed from a substantially rigid material. As shown, a width W6 of the second layer 1406 can be greater than the width WA of the anvil 54. This second layer 1406, 1406' can help prevent stretching of the tissue T near the staples 1008. A third layer 1408, 1408' can be positioned closest to the tissue-contacting surface of the anvil 54 such that the second layer 1406, 1406' is sandwiched between the first and third layers 1402, 1402' and 1408, 1408'. The third layer 1408, 1408' can have a width W7 that is greater than the width WA of the anvil 54, but less than the width W6 of the second layer 1406, as shown. This third layer 1408, 1408' can be semi-rigid to help relieve strain on tissue T as the tissue T expands and contracts. A longitudinal length of the layers can also vary, the length being measured in the direction transverse to the widths. Preferably, the third layer 1408, 1408' has a longest length measured along the longitudinal axis of the anvil 54 compared to a longitudinal length of each of the first and second layers 1402, 1402', 1406, 1406'. As shown in FIG. 34B, multiple adjuncts 1400, 1400', 1400" can be sequentially deployed onto tissue in a row and the longitudinal lengths of the layers can result in regions 1410a, 1410b where the first layer 1402 of one adjunct 1400 overlaps with a first layer 1402' of another adjunct 1400'. In this way, the staples 1008 can still penetrate through these overlapping regions than if multiple, e.g. three or more layers 1402, 1406, 1408 were positioned there. FIG. 33C illustrates two adjuncts 1400, 1400' stapled onto the tissue T at about a 90 degree angle relative thereto, the first adjunct 1400 having a first terminal end and the second adjunct 1400' having a second terminal end. The first and second terminal ends form the overlapping region 1410a, as shown. These adjuncts 1400, 1400' can be used to allow a user to deploy adjuncts to accommodate various geometries of tissue. These multilayer adjuncts 1400, 1400' can vary in any number of ways. While the layers 1402, 1406, 1408 can have various thicknesses, in the illustrated embodiment the second layer 1406 has a smaller thickness than a thickness of each of the first and third layers 1402, 1408. For example, the first layer 1402 can be in the range of about 3 to 15 mm, the second layer 1406 can be in the range of about 5 to 20 mm, and the third layer 1408 can be in the range of about 3 to 20 mm. In certain aspects, these layers 1402, 1404, 1406 and 1402', 1404', 1406' can be laminated together prior to being coupled to the anvil/cartridge assembly 54, 52. In certain aspects, layers 1406 and 1406' may be at least partially comprised of an absorbable material such as PDS®.

Reinforcing Tissue with Sealant and Adjuncts

Any of the adjuncts herein can be used in conjunction with a sealant to help maintain a seal around staples as the tissue expands and contracts following a surgery. A sealant can have various formulations and differing viscosity and curing behavior. Generally, a sealant can be made from a biocompatible and bioabsorbable material that can be configured to transition from a first, liquid state to a second, hardened state via a curing process, such as a polymerization reaction. The first state can be a softened state, e.g., a fluid, a gel, a foam, etc. and the second state can be a hardened state, e.g., a solid, a rigid member, etc. When the sealant is in the first, softened state, the sealant can flow through the delivery tube and into the sealing cuff, as described in greater detail below. The sealant can transition from the first, softened state to the second, hardened state after a predetermined amount of time. In certain aspects, the sealant can be formed from biologic material. In some embodiments, the sealant can assist in wound healing by releasing various chemical compounds, during and/or after curing of the sealant in a patient's body. By way of non-limiting example, the sealant can be configured to release a therapeutic drug, such as promoters of wound healing (e.g., transforming growth factor-beta, etc.), antibacterial agents (e.g., triclosean, ionized silver, etc.), and other known agents over time to aid the tissue in healing near the location of the sealant in a body. In one embodiment, a fibrin sealant can include two reactive components combined immediately prior to delivery into a patient, such as Thrombin and a biologically active component (BAC2), Fibrinogen and Factor XIII In certain aspects, the components can be provided in a 5:1 volumetric ratio of BAC2 to Thrombin. In an alternative embodiment, the material may be the fibrin sealant sold under the trade name Evicel®. In another embodiment, the sealant can be blood, such as autologous blood.

Figure 35A:
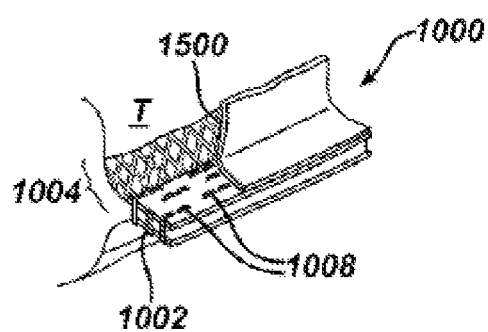
FIG. 35A is a perspective view of first and second adjunct materials stapled onto tissue and having a sealant delivered onto an outer surface of the first adjunct.

FIG. 35A illustrates the adjunct of FIG. 17B having sealant 1500 delivered thereon. As shown, the sealant 1500 can be delivered so that it substantially covers the central 1002 and wing regions 1004 of the adjunct 1000 or in another embodiment (not shown), the sealant 1500 can be selectively delivered onto only the central region 1002 and not onto the wing region 1004.

Figure 35B:
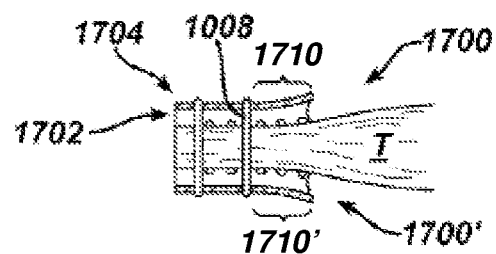
FIG. 35B is a side view of the first and second adjunct materials of FIG. 35A stapled to tissue.
Figure 35C:
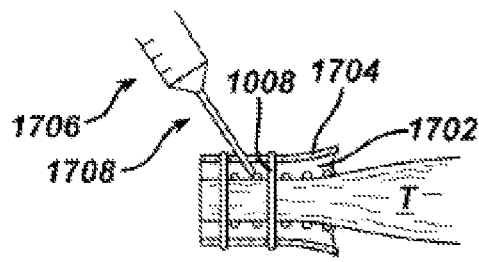
FIG. 35C is a side view of the first and second adjunct materials of FIG. 35A having sealant delivered to a space below an outer surface of the adjunct.
Figure 35D:
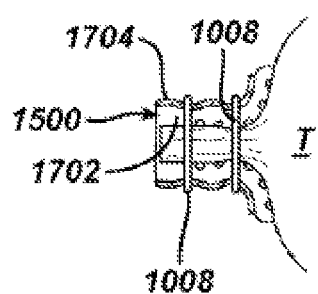
FIG. 35D is a side view of the first and second adjunct materials of FIG. 35A in an expanded position.

The sealant 1500 can be delivered to an adjunct in other ways, and need not be delivered to an outer surface of the adjunct 1000. For example, FIG. 35B illustrates multilayer adjuncts 1700, 1700' stapled onto tissue T. The layers 1702, 1704 can be formed from various materials, but in the illustrated embodiment include a first layer 1702 of fibrous scaffold positioned adjacent to the tissue T and a second layer 1704 consisting of an elastic film. A delivery tool 1706 having an injection needle 1708 can have a sealant 1500 disposed therein and can penetrate into the first layer 1702 of fibrous scaffold. The sealant 1500 can be delivered to this first layer 1702, as in FIG. 35C and the injection needle 1708 can be removed from the patient's body. The sealant 1500 can bind directly onto the tissue T and/or may be held in firm apposition to the tissue by layer 1704, and as in other embodiments, can have a wing region 1710, 1710' that distributes a strain to tissue beyond the staples 1008 at the staple line. When the sealant is Evicel®, the material forms a fibrin clot from fibrinogen. Without a loss in generality, other sealants form a hardened sealing structure by different mechanisms that are useful for sealing leak pathways. The combination of sealant 1500 and adjunct material 1700 can prevent formation of leaks as the tissue T expands and contracts. The adjuncts 1700' and layers 1702', 1704' can be substantially similar to the adjunct 1700 and 1702, 1704 layers previously described.

Figure 36A:
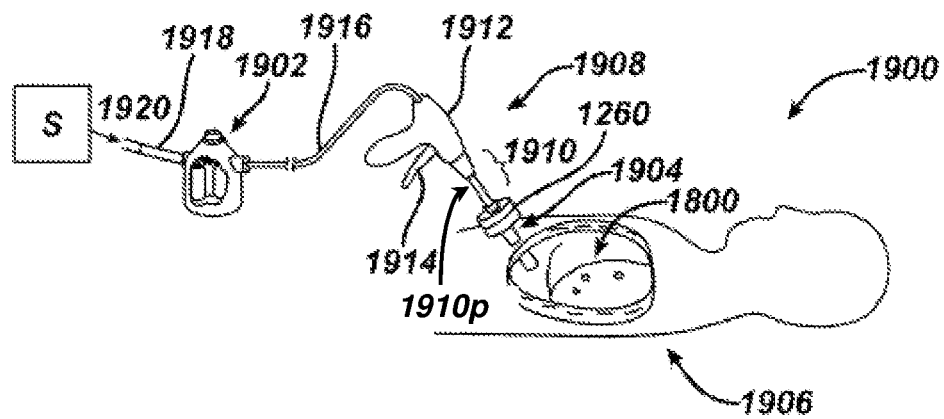
FIG. 36A is a perspective view a system for nebulizing a sealant which includes a container and an applicator tool extending through a trocar and into a patient.
Figure 36B:
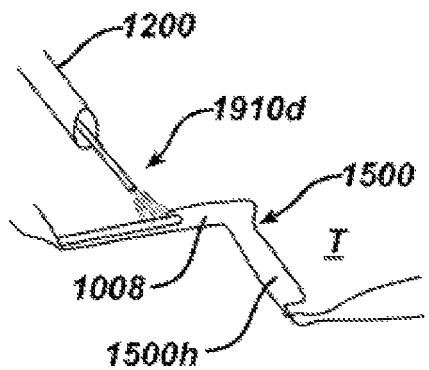
FIG. 36B is perspective view of the applicator tool of FIG. 36A delivering sealant to a staple line in tissue.
Figure 36C:
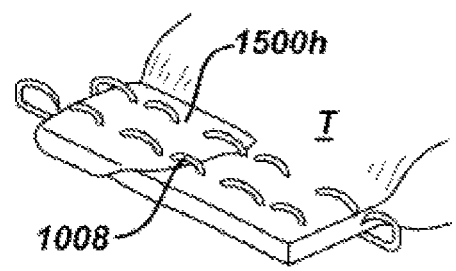
FIG. 36C is a perspective view of the nebulized sealant of FIG. 36A hardened onto the staple line.

A sealant can be used to reinforce tissue in other ways. For example, FIGS. 36A-36C illustrate sealant 1500 being delivered to a chest cavity 1800 of a patient. As shown in FIG. 35A, a system 1900 for delivering a sealant 1500 can include a container or canister 1902 for receiving components A, B, C of a sealant 1500 therein. In certain aspects, the components A, B, C can include acid solubilized collagen A, fibrinogen B, and thrombin C. A trocar 1200 can extend through an incision 1904 formed in a patient 1906 and into the chest cavity 1800. An applicator tool 1908 can have a shaft 1910 extending through the trocar 1200, a distal end 1910*d* of the shaft 1910 terminating in the chest cavity. A handle assembly 1912 can be formed on a proximal end 1910*p* of the shaft 1910 and can be configured to be grasped be a user. The handle assembly 1912 can be a pistol-grip type handle assembly and can include one or more actuators, such as a lever 1914 that can be pivoted to actuate the device 1908. The canister 1902 and the applicator tool 1908 can be coupled together in various ways, such as via a tube 1916. This tube 1916 can be substantially flexible to facilitate movement of the applicator tool 1908 during a procedure. The canister 1902 can have a second tube 1918 coupled thereto and connected to a gas source S so that gas 1920 can be delivered to the canister 1902. The gas 1920 can include, by way of non-limiting example, $CO_2$, $O_2$, etc. In certain aspects, the gas source S can be a continuous gas source such as a continuous $CO_2$ gas source available in hospital operating rooms. One or more valves (not shown) can be disposed in the tube 1916, in the handle assembly 1912, in the shaft 1910, or in any other portion of the system 1900 and can be selectively opened and closed by activating the actuator, such as by pivoting the actuator 1914 on the handle assembly 1912. For example, one valve can control influx of the gas 1920 into the canister 1902 and another valve can control delivery of the sealant 1500 into the applicator tool 1908. After tissue T is stapled, such as by deploying one or more cartridges of staples onto lung tissue, the distal end 1910*d* of the shaft 1910 of the applicator 1908 can be positioned near the staples 1008 as in FIG. 36B. Preferably, the distal end 1910*d* of the applicator tool 1908 is positioned about 5 to 30 mm away from a staple line depending on the size of the region to cover. A user can grasp the handle assembly 1912 of the applicator tool 1908 and activate the actuator 1914, such as by moving the pivotable lever 1914 proximally. This can open a valve disposed in the system 1900 and begin delivering the gas 1920 to the canister 1902 to nebulize the sealant 1500 so that it forms encapsulated liquid droplets that can be sprayed directly onto the tissue T, as shown. In this way, the sealant 1500 can be delivered onto the tissue along the staple line, as shown in FIG. 36C. The sealant 1500 can harden thereon, forming hardened regions 1500*h* facilitating formation and maintenance of a seal along the staples 1008. The sealant 1500 can also be delivered onto an adjunct rather than directly onto the tissue T, such as any of the adjuncts described herein. As will be appreciated by a person skilled in the art, sealant can be delivered to any portion of the tissue, such as only the tissue at the staple line and/or beyond the staple line.

Figure 37A:
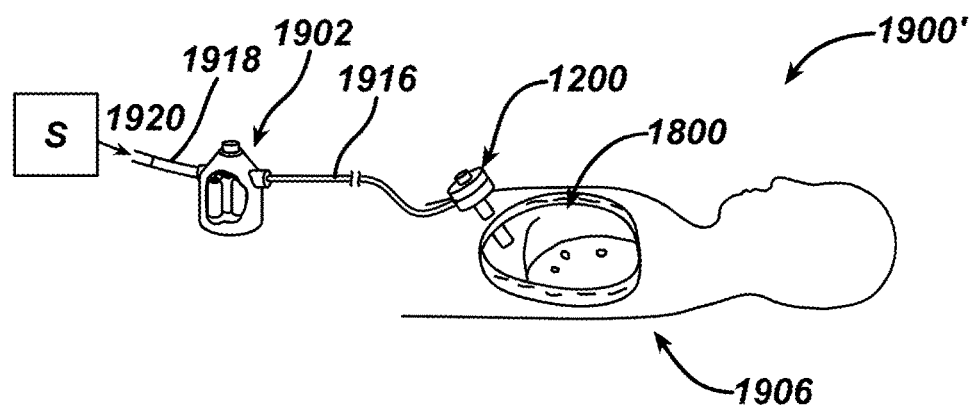
FIG. 37A is a perspective view of another exemplary system for nebulizing a sealant and delivering a nebulized sealant to a patient directly through a trocar and into a patient.
Figure 37B:
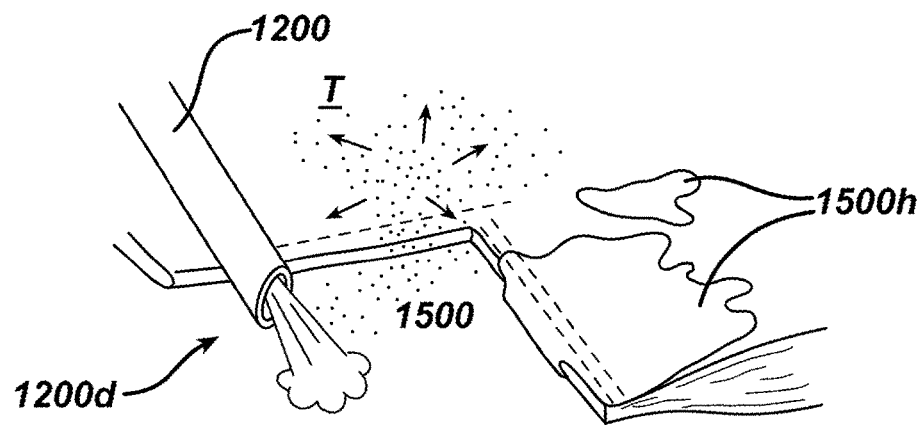
FIG. 37B is a perspective view of the trocar of FIG. 37A delivering nebulized sealant onto tissue at and beyond the staple line.

A sealant can be delivered in various ways. For example, a system 1900' for delivering a sealant 1500 is provided in FIG. 37A and includes many of the features of FIG. 36A, including a gas source, canister, etc. However, in this embodiment the system delivers a nebulized sealant 1500 directly through the trocar 1200 and does not include an applicator tool. In this embodiment, the system also need not include valves and the delivery of the gas 1920 to the canister 1902 can simply be controlled using a valve at the gas source. The delivery of gas into the canister 1902 can also nebulize the sealant 1500, but rather than form encapsulated liquid droplets, the gas 1920 can be delivered at a higher pressure and rate to create a nebulized fog of sealant 1600. As shown in FIG. 37B, this sealant fog 1500 can spread throughout the chest cavity of the patient and can harden on all surfaces of the tissue, such as forming hardened regions 1500*h* along all surfaces of the patient's lungs.

In an embodiment in which the sealant is blood, such as autologous blood, the blood can be harvested from the patient and applied to the adjunct material. By way of non-limiting example, the adjunct material can be ORC, a known hemostatic agent, and the application of the blood to the ORC adjunct will cause the formation of a clot, resulting in an effective sealing structure. A person skilled in the art will appreciate that blood, such as autologous blood can be applied to a variety of adjunct materials to provide an enhanced sealing structure. Further, a person skilled in the art will appreciate that the volume of blood applied to the adjunct will vary depending upon a number of factors, including the type and location of tissue as well, the age and condition of the patient, and the identity of the adjunct. Generally, however, when the adjunct is an ORC material, the blood can be applied in an amount in the range of about 5-10 cc per line of staple used to affix the adjunct to the tissue.

Reprocessing

The devices disclosed herein can be designed to be disposed of after a single use, or they can be designed to be used multiple times. In either case, however, the device can be reconditioned for reuse after at least one use. Reconditioning can include any combination of the steps of disassembly of the device, followed by cleaning or replacement of particular pieces, and subsequent reassembly. In particular, the device can be disassembled, and any number of the particular pieces or parts of the device can be selectively replaced or removed in any combination. Upon cleaning and/or replacement of particular parts, the device can be reassembled for subsequent use either at a reconditioning facility, or by a surgical team immediately prior to a surgical procedure. Those skilled in the art will appreciate that reconditioning of a device can utilize a variety of techniques for disassembly, cleaning/replacement, and reassembly. Use of such techniques, and the resulting reconditioned device, are all within the scope of the present application.

In some embodiments, devices described herein can be processed before surgery. First, a new or used instrument, which can include an adjunct material, is obtained and if necessary cleaned. The instrument can then be sterilized. In some embodiments, the instrument can be dried, e.g., in an oven, together with a desiccant item, which can have a greater affinity for moisture than the adjunct material. In one sterilization technique, the instrument is placed in a closed and sealed container, such as a plastic or TYVEK bag or a foil bag. The container and instrument are then placed in a field of radiation that can penetrate the container, such as gamma radiation, x-rays, or high-energy electrons. The radiation kills bacteria on the instrument and in the container. In another sterilization technique, the instrument is placed in a first container, such as a plastic or TYVEK bag, having a vapor permeable backing. The first container can then be packaged in a second container, e.g., a foil bag, which can be left open. The first and second containers, together with the instrument, can undergo ethylene oxide sterilization. The second container can then be sealed to prevent moisture exposure. Prior to sealing, a desiccant item may be included in at least one of the first and second containers to further prevent changes to one or more device components. In both techniques, the sterilized materials can then be stored in the sterile container(s) to keep the materials sterile until the container(s) is/are opened in the medical facility.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. A method for implanting a tissue reinforcement material onto tissue, comprising;
    engaging tissue between a cartridge assembly and an anvil of a surgical stapler at a surgical site in a body of the patient, only one of the cartridge assembly and the anvil having a tissue reinforcement material disposed thereon, the tissue reinforcement material including a central region and an outer region adjacent to the central region and defining an edge of the tissue reinforcement material;
    actuating the surgical stapler to eject a plurality of staples from the cartridge assembly and into the central region, but not the outer region, so as to form a staple line through the central region and into the tissue to hold the tissue reinforcement material at the surgical site and seal around each of the plurality of staples;
    introducing a tool separate from the surgical stapler into the body of the patient; and
    after actuating the surgical stapler, delivering sealant from the tool to the central region, but not the outer region, of the tissue reinforcement material when the sealant is in a first, liquid state such that the sealant solidifies on the central region of the tissue reinforcement material and reinforces the seal around the staples and such that the outer region that to adjacent to the central region is free of sealant.

2. The method of claim 1, further comprising inserting the cartridge assembly and the anvil into the surgical site with the outer region of the tissue reinforcement material folded around the one of the cartridge assembly and the anvil having the tissue reinforcement material disposed thereon.

3. The method of claim 1, wherein actuating the surgical stapler releases the tissue reinforcement material from the surgical stapler.

4. The method of claim 3, wherein actuating the surgical stapler advances a cutting member through the central region of the tissue reinforcement material.

5. The method of claim 1, wherein the tool includes an applicator tool, and the sealant is delivered through the applicator tool positioned adjacent to the tissue reinforcement material.

6. The method of claim 1, wherein the surgical stapler forms a staple line having at least two rows of staples.

7. The method of claim 1, wherein as the sealant is delivered to the tissue reinforcement material in the first, liquid state, the sealant penetrates a space in the tissue at the staple line and solidifies therein.

8. The method of claim 1, wherein the sealant comprises a mixture of collagen, fibrinogen, and thrombin.

9. The method of claim 1, wherein the sealant transitions from the first, liquid state to a second, solid state after a predetermined amount of time.

10. The method of claim 1, wherein the solidified sealant is bioabsorbed after a predetermined passage of time.

11. The method of claim 1, wherein the tool includes an injection needle that injects the sealant into the body of the patient.

12. The method of claim 1, wherein the tool includes an applicator tool including an actuator at a proximal handle portion of the applicator tool, and actuating the actuator causes the sealant to be delivered from the applicator tool.

13. The method of claim 1, wherein the central region is substantially solid, and the outer region is mesh.

14. A method for implanting a tissue reinforcement material onto tissue, comprising;
    engaging tissue between a cartridge assembly and an anvil of a surgical stapler at a surgical site, at least one of the cartridge assembly and the anvil having a tissue reinforcement material retained thereon, the tissue reinforcement material including an inner layer including a fibrous scaffold having a first surface configured to engage the tissue, and the tissue reinforcement material including an outer layer including a film attached to a second surface of the fibrous scaffold that is opposite to the first surface;
    actuating the surgical stapler to eject the staples from the cartridge assembly to hold the tissue reinforcement material at the surgical site, the staples piercing holes in the tissue reinforcement material and the tissue;
    after actuating the surgical stapler, penetrating the inner and outer layers of the tissue reinforcement material with an injection needle of a delivery tool; and
    delivering sealant to the inner layer of the tissue reinforcement material through the injection needle when the sealant is in a first, liquid state such that the sealant solidifies and seals the holes.

15. A method for implanting a tissue reinforcement material onto tissue, comprising;
    engaging tissue between a cartridge assembly and an anvil of a surgical stapler at a surgical site in a body of the patient, at least one of the cartridge assembly and the anvil having a tissue reinforcement material retained thereon, the tissue reinforcement material including a central region and an outer region adjacent to the central region and defining an edge of the tissue reinforcement material, wherein the central region is a film and the outer region is a mesh;
    actuating the surgical stapler to eject a plurality of staples from the cartridge assembly and into the central region, but not the outer region, so as to form a staple line through the central region and into the tissue to hold the tissue reinforcement material at the surgical site and seal around each of the plurality of staples;
    introducing a tool separate from the surgical stapler into the body of the patient; and
    after actuating the surgical stapler, delivering sealant from the tool to the central region, but not the outer region, of the tissue reinforcement material when the sealant is in a first, liquid state such that the sealant solidifies on the central region of the tissue reinforcement material and reinforces the seal around the staples and such that the outer region is free of sealant.

16. The method of claim 15, further comprising inserting the cartridge assembly and the anvil into the surgical site with the outer region of the tissue reinforcement material folded around at least one of the cartridge assembly and the anvil.

17. The method of claim 15, wherein actuating the surgical stapler releases the tissue reinforcement material from the surgical stapler.

18. The method of claim 17, wherein actuating the surgical stapler advances a cutting member through the central region of the tissue reinforcement material.

19. The method of claim 15, wherein as the sealant is delivered to the tissue reinforcement material in the first, liquid state, the sealant penetrates a space in the tissue at the staple line and solidifies therein.

20. The method of claim 15, wherein the tissue reinforcement material includes a first tissue reinforcement material retained on the cartridge assembly and a second tissue reinforcement material retained on the anvil, and delivering the sealant from the tool to the tissue reinforcement material includes delivering the sealant to each of the first and second tissue reinforcement materials.

\* \* \* \* \*